United States Patent [19]
Olszewski et al.

[11] Patent Number: 5,912,415
[45] Date of Patent: Jun. 15, 1999

[54] ARABIDOPSIS SPINDLY GENE, METHODS OF IDENTIFICATION AND USE

[75] Inventors: Neil E. Olszewski, Roseville, Minn.; Steven E. Jacobsen, Pasadena, Calif.

[73] Assignee: Regents of the University of Minnesota, Minn.

[21] Appl. No.: 08/649,046

[22] Filed: May 16, 1996

[51] Int. Cl.$^6$ .............................. A01H 5/00; C12N 15/82; C12N 15/63; C07H 21/04

[52] U.S. Cl. ........................ 800/298; 435/320.1; 435/419; 536/23.6

[58] Field of Search .............................. 435/172.3, 320.1, 435/419; 800/205; 536/23.6

[56] References Cited

FOREIGN PATENT DOCUMENTS

| 0 692 537 | 1/1996 | European Pat. Off. . |
|---|---|---|
| WO 93/16096 | 8/1993 | WIPO . |
| WO 94/28141 | 12/1994 | WIPO . |
| WO 95/35383 | 12/1995 | WIPO . |
| WO 96/05317 | 2/1996 | WIPO . |

OTHER PUBLICATIONS

Jacobsen et al., "SPINDLY, a tetratricopeptide repeat protein involved in gibberellin signal transduction in Arabidopsis," *Proc. natl. Acad. Sci. USA*, 93, 9292–9296 (1996).

Jacobsen et al., "*Arabidopsis thaliana* gibberellin signal transduction protein, (SPINDLY) mRNA, complete cds, "*EMBL Sequence Database*, Rel. 49, Accession No. U62135 (1996).

Newman et al., "15212 *Arabidopsis thaliana* cDNA clone 183F13T7," *EMBL Sequence Database*, Rel. 44, Accession No. H37083 (1995).

Newman et al., "17280 *Arabidopsis thaliana* cDNA clone 204H23T7," *EMBL Sequence Database*, Rel. 45, Accession No. H76849 (1995).

Walbot, "Strategies for Mutagenesis and Gene Cloning Using Transposon Tagging and T–DNA Insertional Mutagenesis," *Annu. Rev. Plant Physiol. Plant Mol. Biol.*, 43 (1), 49–82 (1992).

Wilson et al., "Phenotype Suppression of the Gibberellin–Insensitive Mutant (*gai*) of Arabidopsis," *Plant. Physiol.*, 108, 495–502 (1995).

Wilson et al., "*Caenorhabditis elegans* cosmid K04G7," *EMBL Sequence Database*, Rel. 43, Accession No. U21320 (1995).

Steven E. Jacobsen et. al., "Molecular Characterization of Spy: A Gene Involved in Response to Gibberellins", $6^{th}$ *International Meeting on Arabidopsis Research* Abstract, 308, Jun. 7–11, 1995.

Steven E. Jacobsen et. al., "Molecular Characterization of Spy: A Gene Involved in Response to Gibberellins", $15^{th}$ *International Conference on Plant Growth Substances* Abstract No. 018, Jul. 14–18, 1995.

Steven E. Jacobsen et. al., "Molecular Characterization of Spy: A Gene Involved in Response to Gibberellins", *Supplement to Plant Physiology*, 108 (2), Abstract No. 159, 1995.

Steven E. Jacobsen et. al., "Mutations at the Spindly Locus of Arabidopsis Alter Gibberellin Signal Transduction", *The Plant Cell*, 5, 887–896, 1993.

Kenneth A. Feldman, "T–DNA Insertion Mutagenesis in Arabidopsis: Mutational Spectrum", *The Plant Journal*, 1 (1), 71–82, 1991.

Kenneth A. Feldman, "T–DNA Insertion Mutagenesis in Arabidopsis: Seed Infection/Transformation", *Methods In Arabidopsis Research*, Chapter 10, 274–289, eds. C. Koncz et. al., 1992.

M. Koornneef et. al., "Induction and Analysis of Gibberellin Sensitive Mutants in *Arabidopsis thaliana* (L.) Heynh", *Theoretical and Applied Genetics*, 58, 257–263, 1980.

M. Koornneef et. al., "A Gibberellin Insensitive Mutant of *Arabidopsis thaliana*", *Physiologia Plantarum*, 65, 33–39, 1985.

John R. Lamb et. al., "Tetratrico Peptide Repeat Interactions: To TPR or Not to TPR?", *Trends in Biochemical Sciences*, 20, No. 7, 257–259, 1995.

Paul W. Oeller et. al., "Reversible Inhibition of Tomato Fruit Senescence by Antisense RNA", *Science*, 254, No. 5030, 437–439, 1991.

Neil E. Olszewski et. al., "Specialized Binary Vector for Plant Tranformation: Expression of the *Arabidopsis Thaliana* AHAS Gene in *Nicotiana Tabacum*", *Nucleic Acids Research*, 16 (22), 10765–10782, 1988.

Stewart B. Rood et. al., "Gibberellins: A Phytohormonal Basis for Heterosis in Maize", *Science*, 242, No. 4870, 1216–1218, 1988.

R.S. Sikorski et. al., "TPR Proteins as Essential Components of the Yeast Cell Cycle", *Cold Spring Harbor Symposia on Quantitative Biology*, The Cell Cycle, LVI, 663–673, 1991.

Jorge Hernández Torres et. al., "Isolation and Characterization of *gmsti*, A Stress–Inducible Gene From Soybean (*Glycine Max*) Coding For a Protein Belonging to the TPR (*Tetratrico*peptide repeats) Family", *Plant Molecular Biology*, 27 (6), 1221–1226, 1995.

Marguerite J. Varagona et. al., "Monocot Regulatory Protein Opaque–2 Is Localized in the Nucleus of Maize Endosperm and Transformed Tobacco Plants", *The Plant Cell*, 3, 105–113, 1991.

Napoli et al. Introduction of a chimeric chalcone synthase gene into petunia results in reversible co–suppression of homologous genes in trans. The Plant Cell. 2:279–289, Apr. 1990.

Smith et al. Antisense RNA inhibition of polygalacturonase gene expression in transgenic tomatoes. Nature. 334:724–726, Aug. 1988.

*Primary Examiner*—Douglas W. Robinson
*Assistant Examiner*—Thanda Wai
*Attorney, Agent, or Firm*—Mueting, Raasch & Gebhardt, P.A.

[57] ABSTRACT

This invention relates to the identification of a gene involved in the gibberellin signal transduction pathway. Mutations to this gene mimic the effect of gibberellin treatment and transgenic plants expressing the gene correct a spindly phenotype. Methods are disclosed for isolating and using the gene from a variety of plants.

23 Claims, 10 Drawing Sheets

FIGURE 2

Sequence of the SPY Protein

| | |
|---|---|
| MVGLEDDTERERSPVVENGFSNGSRSSSSSAGVLSPSRKVTQGNDTLSYA | 50 |
| NILRARNKFADALALYEAMLEKDSKN | 76 |

| | |
|---|---|
| VEAHIGKGICLQTQNKGNLAFDCFSEAIRLDPHN | 110 |
| ACALTHCGILHKEEGRLVEAAESYQKALMADASYKPAAECL | 151 |
| AIVLTDLGTSLKLAGNTQEGIQKYYEALKIDPHY | 185 |
| APAYYNLGVVYSEMMQYDNALSCYEKAALERPMY | 219 |
| AEAYCNMGVIYKNRGDLEMAITCYERCLAVSPNFEIAKNNM | 260 |
| AIALTDLGTKVKLEGDVTQGVAYYKKALYYNWHY | 294 |
| ADAMYNLGVAYGEMLKFDMAIVFYELAFHFNPHC | 328 |
| AEACNNLGVLYKDRDNLDKAVECYQMALSIKPNF | 362 |
| AQSLNNLGVVYTVQGKMDAAASMIEKAILANPTY | 396 |
| AEAFNNLGVLYRDAGNITMAIDAYEECLKIDPDS | 430 |

```
 A  A    NLGV  YK  G      A    YE AL      P Y    Consensus
```

| | |
|---|---|
| RNAGQNRLLAMNYINEGLDDKLFEAHRDWGWRFTRLHPQYTSWDNLKDPE | 480 |
| RPITIGYISPDFFTHSVSYFIEAPLTHHDYTKYKVVVYSAVVKADAKTYR | 530 |
| FRDKVLKKGGVWKDIYGIDEKKIASMVREDKIDILVELTGHTANNKLGTM | 580 |
| ACRPAPVQVTWIGYPNTTGLPTVDYRITDSLADPPDTKQKQVEELVRLPD | 630 |
| CFLCYTPSPEAGPVCPTPALSNGFVTFGSFNNLAKITPKVLQVWARILCA | 680 |
| VPNSRLVVKCKPFCCDSIRQRFLTTLEQLGLESKRVDLLPLILFNHDHMQ | 730 |
| AYSLMDISLDTFPYAGTTTTCESLYMGVPCVTMAGSVHAHNVGVSLLTKV | 780 |
| GLGHLVAKNEDEYVQLSVDLASDVTALSKLRMSLRDLMAGSPVCNGPSFA | 830 |
| VGLESAYRNMWKKYCKGEVPSLRRMEMLQKEVHDDPLISKDLGPSRVSVT | 880 |
| GEATPSLKANGSAPVPSSLPTQSPQLSKRMDSTS | 914 |

FIGURE 3A

Sequence of the SPY cDNA

```
   1  GGAGAGCTAA TCTGAGTCGT TGCCTCTGTC CACTGGCTCG GACCGACCTC
  51  GTACCTCTTT CATTTGTCCT CGAGCTTATA ATAGAGGCTA CGCGTCGCCG
 101  CCACCTCCGC TCCATCCATT CACGGCCAAG CGACGACTCC ACCGCTTAGG
 151  CTTGGCGTCT GAGGTATACT GATCAACGCT TTCTGTTTTC GGAGGAGCGA
 201  GGCGAGATCA GCTTCTCTTA TGTCTACTCA ACATATCAT  TCTTCTTTAG
 251  CCACTCGATT TCTTCTCTAG CGGCTCCAGA GGTTTCGTCG CTACAGAGTC
 301  AAGTTCCTCT TTTCAGGTTT TGTGGTGAAC AAGATTTTAG TTACAAAAAA
 351  ATGGTGGAC  TGGAAGATGA TACTGAGAGA GAGAGGTCAC CAGTCGTAGA
 401  GAATGGTTTT TCCAATGGGT CTCGGTCTTC TTCTTCTAGC GCAGGTGTTT
 451  TGTCTCCATC ACGAAAGGTC ACTCAGGGGA ACGATACACT TTCTTATGCC
 501  AATATTCTTC GGGCAAGAAA CAAGTTTGCT GATGCGCTTG CTCTCTATGA
 551  GGCTATGCTG GAGAAAGATA GCAAGAATGT TGAAGCTCAC ATTGGAAAAG
 601  GGATATGCTT GCAGACGCAG AACAAAGGGA ATCTAGCTTT CGATTGTTTT
 651  TCTGAAGCGA TCAGGTTGGA TCCGCATAAT GCTTGTGCCC TTACACACTG
 701  TGGTATACTT CATAAAGAAG AAGGACGCCT CGTAGAAGCT GCTGAGTCCT
 751  ACCAGAAAGC ATTGATGGCA GATGCATCAT ACAAGCCAGC AGCAGAGTGT
 801  TTAGCCATTG TTTTGACCGA CCTTGGAACT AGCCTGAAGC TGGCTGGGAA
 851  TACTCAGGAA GGAATTCAAA AGTATTACGA AGCCCTTAAG ATTGACCCAC
 901  ACTATGCTCC TGCATATTAC AACTTAGGTG TTGTATACTC CGAAATGATG
 951  CAATATGACA ATGCCTTGAG CTGCTACGAG AAGGCTGCAC TTGAGAGGCC
1001  TATGTATGCT GAAGCATATT GTAACATGGG TGTCATTTAT AAGAACCGTG
1051  GTGACTTGGA GATGGCAATC ACTTGTTATG AGAGATGTCT AGCTGTGTCT
1101  CCAAACTTTG AGATTGCGAA GAACAATATG GCCATAGCTC TGACAGATTT
1151  AGGAACAAAG GTTAAACTTG AAGGCGATGT AACCCAAGGA GTGGCATATT
1201  ACAAGAAGGC TCTCTATTAT AACTGGCACT ATGCAGATGC TATGTACAAT
1251  CTTGGGGTGG CTTATGGAGA AATGCTAAAG TTCGACATGG CGATTGTCTT
```

FIGURE 3B

```
1301  CTATGAGCTT GCTTTCCACT TTAATCCACA TTGTGCTGAG GCTTGCAACA
1351  ATTTGGGAGT ACTTTACAAA GACCGTGACA ACCTTGATAA AGCTGTGGAG
1401  TGTTATCAGA TGGCTCTATC AATCAAACCA AATTTTGCAC AGTCGCTTAA
1451  TAACCTTGGT GTCGTCTATA CAGTCCAGGG GAAAATGGAT GCTGCTGCCA
                                     A (spy-1)
1501  GCATGATTGA GAAGGCTATA CTTGCTAATC CCACATATGC AGAAGCTTTT
1551  AACAACCTAG GTGTTCTTTA CAGAGATGCT GGAAATATAA CTATGGCTAT
1601  CGATGCTTAT GAGGAATGCC TTAAGATAGA TCCAGATTCT CGCAATGCTG
1651  GCCAGAACCG ATTGCTTGCC ATGAATTACA TAAATGAAGG ACTCGATGAC
1701  AAACTATTTG AGGCTCACAG AGACTGGGGT TGGCGCTTCA CAAGATTACA
1751  CCCTCAATAC ACTTCATGGG ATAATCTGAA AGATCCAGAG CGACCTATCA
1801  CCATTGGATA TATCTCACCA GATTTCTTCA CTCATTCAGT ATCTTATTTC
1851  ATTGAAGCTC CCCTTACGCA TCATGATTAT ACAAAGTACA AAGTGGTGGT
1901  TTATTCAGCG GTAGTTAAGG CAGATGCAAA ACATACAGG TTTAGGGATA
1951  AAGTGTTGAA GAAAGGTGGA GTTTGGAAGG ATATATACGG GATAGATGAG
2001  AAAAAGATAG CAAGTATGGT CAGAGAGGAC AAAATCGACA TTTTGGTAGA
2051  ACTCACTGGT CATACGGCAA ACAACAAGTT GGGAACAATG GCCTGCAGAC
2101  CAGCACCGGT TCAGGTTACT TGGATCGGCT ATCCAAATAC TACGGGTTTG
                                     A (spy-3)
2151  CCCACTGTTG ATTACAGAAT TACAGATTCG TTGGCTGATC CACCAGATAC
2201  CAAACAAAAG CAGGTCGAGG AGCTGGTTAG GCTTCCGGAC TGTTTTCTTT
2251  GTTATACACC TTCCCCAGAG GCTGGTCCTG TTTGTCCAAC ACCTGCGCTT
2301  TCTAATGGCT TTGTCACATT TGGTAGTTTC AACAACCTCG CAAAGATAAC
2351  TCCTAAGGTG CTGCAAGTGT GGGCTAGGAT ACTGTGTGCA GTTCCCAATT
2401  CTCGTCTAGT GGTAAAATGC AAACCTTTCT GCTGCGATAG CATTAGGCAG
2451  AGGTTTCTCA CCACGCTGGA GCAGCTTGGG TTAGAATCAA AGCGTGTTGA
2501  TCTCTTGCCT CTGATTCTTT TCAATCACGA CCATATGCAA GCCTATTCCT
2551  TGATGGATAT TAGTTTGGAC ACATTCCCTT ATGCTGGAAC TACCACTACC
```

FIGURE 3C

```
2601  TGTGAGTCTC TCTACATGGG AGTTCCATGT GTTACAATGG CTGGCTCAGT

2651  ACATGCTCAT AATGTTGGTG TCAGTCTTCT CACTAAAGTT GGATTAGGAC

2701  ACCTGGTTGC CAAAAATGAG GATGAGTATG TTCAGCTATC TGTTGATCTA

2751  GCCTCTGATG TCACAGCTCT TTCTAAATTG AGAATGAGTC TCCGGGATCT

2801  AATGGCTGGA TCTCCTGTTT GTAATGGTCC TTCCTTTGCT GTTGGTCTTG

2851  AATCCGCATA TCGGAATATG TGGAAAAGT ACTGCAAAGG TGAAGTGCCG
                                              A (spy-5)
2901  TCCTTAAGGC GAATGGAAAT GCTGCAAAAA GAGGTCCATG ATGATCCCTT

2951  AATCTCAAAA GACTTGGGAC CATCAAGAGT CAGCGTTACT GGAGAAGCCA

3001  CTCCGTCTCT CAAGGCCAAT GGTTCTGCTC CTGTACCTTC CTCTTTACCA

3051  ACCCAATCCC CGCAGCTCTC AAAGAGAATG GACTCCACTA GCTAGATAAC

3101  CAGCAAATCG AGCTGCTGCG AAATGCCGGC AGAGAGTCTT GACCCATCTG

3151  GAAAGGTGT GAAAGAAAGA GTCGATGAGC TTTTCCTGCT ATTTACTTCC

3201  AAGACAATAG GAACTAGACT TTAGATTACT GCTTGTGTAG TAAAAAGAAT

3251  AGTAAAACCA GCTCTTTCTT TTGTTGTATC TCTTTCTACT CTTAGTTTAG

3301  CTTTACATGA TTCTTGGGAA GTCGTTAGGT GGTAGTGGAT TTGGAGTTTT

3351  TCTTCTCATT TGAGAGATCA AGTTGTTGTG TATCGATTAG GGTTTTAAGG

3401  CTTTTTAGGA TGTTTTCATG TGTTGGATTT TGACTCATAT GATAGTAAAT

3451  ATAGTTATAG AAAGCTTTTC GGTGCC
```

FIGURE 4A

Sequence of the SPY Genomic Region

```
   1   TCTAGACTAG TTTCATAGTC CATGAAAAAA ACATCAAATC TCCTAAATGG
  51   CTGGACATAA TTCAGATGAT TTTGTATGAA ATAAAACATA AAACATATAT
 101   TTTCTTGCAT ATCTGGAGAT TTTTGTTTCT TTATTACAAT GACTAATTAA
 151   TTTACCTTGT TCCTTTTTAT TTTTGCAAAA TGATTACTGT TATCTATTTT
 201   GTCCGTTTCT AATAAAATAA AATAACAATC TGAGCTGTGG AAAGAAAAAA
 251   AAAGGAAAAG CGAGGAGAGC TAATCTGAGT CGTTGCCTCT GTCCACTGGC
 301   TCGGACCGAC CTCGTACCTC TTTCATTTGT CCTCGAGCTT ATAATAGACG
 351   TACGCCGTCG CCGCCACCTC CGCTCCATCC ATTCACGGCC AAGCGACGAC
 401   TCCACCGCTT AGGCTTGGCG TCTGAGGTAT ACTGATCAAC GCTTTCTGTT
 451   TTCGGAGGAG CGAGGCGAGA TCAGCTTCTC TTATGTCTAC TCAAACATAT
 501   CATTCTTCTT TAGCCACTCG ATTTCTTCTC TAGCGGCTCC AGAGGTTTCG
 551   TCGCTACAGA GTCAAGTTCC TCTTTTCAGG TTTTGTGGTA AGTAATCGTT
 601   AAACCCTAAG TATCGGACCT TGTTGTTTAA TCTGTTCGTG TTTACTCTCA
 651   ATTACATATG CATTCTTCTG CTTAATCGTT TCTTTTAGTT TAATTTCTAG
 701   GGTTTACATC CCAAAGGTCT GATCTTTTTG CATATTTGTG TGAATCTTAG
 751   TTTTTTTTTT TTTTTTTGGA ATTGAATGTG ATGAGTTGGG TTTGATACTG
 801   TTAAAGATCA AATCTTTAGC TTCGTTGAAG CTTCATATTT ATGTCAACAA
 851   TGCAAGGTTT ATTTTTCTTC CACCTTTGAT TTGATATTTA TAATTGTTTC
 901   TTTGAAGGTG AACAAGATTT TAGTTACAAA AAAATGGTGG GACTGGAAGA
 951   TGATACTGAG AGAGAGAGGT CACCAGTCGT AGAGAATGGT TTTTCCAATG
1001   GGTCTCGGTC TTCTTCTTCT AGCGCAGGTG TTTTGTCTCC ATCACGAAAG
1051   GTCACTCAGG GGAACGATAC ACTTTCTTAT GCCAATATTC TTCGGGCAAG
1101   AAACAAGTTT GCTGATGCGC TTGCTCTCTA TGAGGCTATG CTGGAGAAAG
1151   ATAGCAAGAA TGTTGAAGCT CACATTGGAA AAGGGATATG CTTGCAGACG
1201   CAGAACAAAG GGAATCTAGC TTTCGATTGT TTTTCTGAAG CGATCAGGTT
1251   GGATCCGCAT AATGCTTGTG CCCTTACACA CTGTGGTATA CTTCATAAAG
1301   AAGAAGGACG CCTCGTAGAA GCTGCTGAGG TGCAACATTA CATTACCTTC
1351   TATCTGTGAT GATTTGCATT AGAGGGTGCT GCATTAGTTA GACCATTGAA
1401   CTTGTTAAAT TGGTGATATG CAATTATGCA TTAGGTTTTT TGCTAGGTAA
1451   TCAGTTTCTA ACGATTAATC ATCATATTTT GCACAGTCCT ACCAGAAAGC
1501   ATTGATGGCA GATGCATCAT ACAAGCCAGC AGCAGAGTGT TTAGCCATTG
1551   TTTTGACCGA CCTTGGAACT AGCCTGAAGC TGGCTGGGAA TACTCAGGAA
1601   GGAATTCAAA AGTATTACGA AGCCCTTAAG ATTGACCCAC ACTATGCTGT
1651   AATTTTCTGT TCCTCTACCA TTTCACACTC TTGGTACCAT TTAACTGATT
1701   CTCTAATTCA GTATGTTATA ATATATTTAT GCAGCCTGCA TATTACAACT
1751   TAGGTGTTGT ATACTCCGAA ATGATGCAAT ATGACAATGC CTTGAGCTGC
1801   TACGAGAAGG CTGCACTTGA GAGGCCTATG TATGCTGAAG CATATTGTAA
1851   CATGGGTGTC ATTTATAAGA ACCGTGGTGA CTTGGAGATG GCAATCACTT
1901   GTTATGAGAG GTAGCATATC TGTTAATTCA TCTCTAACTG TTGACTGGTT
1951   TCTTGCTACT TTGTTGAACG TGCAAGTAAG GCGCTGATTT TTTTCTCTTC
2001   TTCTTCTGCC TTTAGATGTC TAGCTGTGTC TCCAAACTTT GAGATTGCGA
2051   AGAACAATAT GGCCATAGCT CTGACAGATT TAGGAACAAA GGTAAGAATC
2101   CTTAAATTTT ATCACAATTT ATAACTCAAG TATACTTTTT GTAAGGGCG
2151   CCTTCTGGAA AATTCGTTAT AAAACTTCGT TTTGTTTAGC TCCCCTTTGT
2201   GCTGTGTGTG CTTTGTACTT ATGTCACGGC AATGGCATTG GAATCTGTTT
2251   ATGTTCTTTA CTAGTGAACT TTTGCGCTGA ATAATTTTGA TTTGCAGTTT
2301   CTTAATCCTT CTTTTCCATT GGCGAGAAGC TGTTCAGCTG TGAGTACATC
2351   TGACTTGTCA AATGTCAATG ATATTTCAGG TTAAACTTGA AGGCGATGTA
2401   ACCCAAGGAG TGGCATATTA CAAGAAGGCT CTCTATTATA ACTGGCACTA
2451   TGCAGATGCT ATGTACAATC TTGGGGTGGC TTATGGAGAA ATGCTAAAGT
2501   TCGACATGGT ATTTAATTTG TGATTTGTTC ATTTCTGTAA GTCAGTAATG
```

FIGURE 4B

```
2551  GTGTGGTTGT TATCGCGTGT TTATCCTTTC CTCGCCACTT TACTCGCTTG
2601  ATAAAATGAT ATATATCTTG ACTAGTTTAT CTACCTAGAT TTTTATCCTT
2651  CTCCACATGT TCTCGTAATT AATCCAAAAC TCTGTATGTA GATCTCTATA
2701  TTATAATGGA ATTGTAGAGC CAAAGAATGA AATATGTCTG TGGTCATGAT
2751  TGCATTCTCA ATGTGCAGGC GATTGTCTTC TATGAGCTTG CTTTCCACTT
2801  TAATCCACAT TGTGCTGAGG CTTGCAACAA TTTGGGAGTA CTTTACAAAG
2851  ACCGTGACAA CCTTGATAAA GCTGTGGAGT GTTATCAGGT AATATTTTTG
2901  CAGATATCTG TAGCGTTTCA TGAGAATTTC ATTGTGTTTG GTGGCTTATT
2951  ATATCTCCCA ACCTATGTAG ATGGCTCTAT CAATCAAACC AAATTTTGCA
3001  CAGTCGCTTA ATAACCTTGG TGTCGTCTAT ACAGTCCAGG TTTGATATAT
3051  ATTAAGGGCG GCTTAATGTT TTCTTAATTG AATCTCCTAA GTCGATAGAA
3101  TGCCAATTCC TCTGATATTA CAGGGGAAAA TGGATGCTGC TGCCAGCATG
3151  ATTGAGAAGG CTATACTTGC TAATCCCACA TATGCAGAAG CTTTTAACAA
3201  CCTAGGTCTG TTTTCTCATC TTCTGTTCTT TACGAGCTTC CTCACGTGTT
3251  ACAACTGCTT AGAAACTATA TTCCTTTGAA ATTTAGATTT TATGTTTGTC
3301  CTTTTGTTTC TACCTCCCTG GCGCTAAGAG TCTTGTAGTG TCTGTGATAA
3351  CCAGTTTCAT GGTGCGATTC AAATGTAGGT GTTCTTTACA GAGATGCTGG
3401  AAATATAACT ATGGCTATCG ATGCTTATGA GGAATGCCTT AAGATAGATC
3451  CAGATTCTCG CAATGCTGGC CAGGTATCTA TACTTTAGCG TGGTCTTCTT
3501  GTTATGAGGT TGAAAGATAT ATGTGTTTAA AACCTTCTTG TCCCCTTTTG
3551  TAGAACCGAT TGCTTGCCAT GAATTACATA AATGAAGGAC TCGATGACAA
3601  ACTATTTGAG GCTCACAGGT AAGCACATAT ATTATTAATG TAGATTTGTA
3651  TTATGTTGCT TTTATGGGTC TTACAGTGAA AAAATCTTCT GAACACAGAG
3701  ACTGGGGTTG GCGCTTCACA AGATTACACC CTCAATACAC TTCATGGGAT
3751  AATCTGAAAG ATCCAGAGCG ACCTATCACC ATTGGATATA TCTCACCAGA
3801  TTTCTTCACT CATTCAGTAT CTTATTTCAT TGAAGCTCCC CTTACGCATC
3851  ATGATTATAC AAAGTACAAA GTGGTGGTTT ATTCAGCGGT AGTTAAGGTA
3901  GGATTTTTAC CTATATAACT TATATAGATA CATTTTCCCT CTAAGCAATT
3951  CATTTCCTGG TTCTCGTGGC ATTTTTCCCT TTTGAGCAAT CATTGGTCTC
4001  TCATGGCTTT GCAGGCAGAT GCAAAACAT  ACAGGTTTAG GGATAAAGTG
4051  TTGAAGAAAG GTGGAGTTTG GAAGGATATA TACGGGATAG ATGAGAAAAA
4101  GATAGCAAGT ATGGTCAGAG AGGACAAAAT CGACATTTTG GTAGAACTCA
4151  CTGGTCATAC GGCAAACAAC AAGTTGGGAA CAATGGCCTG CAGACCAGCA
4201  CCGGTTCAGG TGAGAGGATA TATTAAACCT ATCTCATTTT GTTGTTTCGG
4251  GTTTTGCCTT TGACTTTCCA TTTCAAGTGT ACTTATATTG GCTAAGATAC
4301  CAGGTTACTT GGATCGGCTA TCCAAATACT ACGGGTTTGC CCACTGTTGA
4351  TTACAGAATT ACAGATTCGT TGGCTGATCC ACCAGATACC AAACAAAAGT
4401  ACGTTTTGGT TCAAGATGCA ATTTTGGGTT TCGGAAGTGC TCCAAATAAA
4451  AATCTTAATT TTTATTTATT TATTTTGTGA TATTTGATTG CAGGCAGGTC
4501  GAGGAGCTGG TTAGGCTTCC GGACTGTTTT CTTTGTTATA CACCTTCCCC
4551  AGAGGCTGGT CCTGTTTGTC CAACACCTGC GCTTTCTAAT GGCTTTGTCA
4601  CATTTGGTAG TTTCAACAAC CTCGCAAAGG TTAAAAAATT TGTGTCCTTG
4651  GATTATGCAC ACCAATCTCC CCTAGTATCT CTTTCAATGT TTTGACAGGT
4701  TTATCTCTGT TTGTGCAAAT CAGATAACTC CTAAGGTGCT GCAAGTGTGG
4751  GCTAGGATAC TGTGTGCAGT TCCCAATTCT CGTCTAGTGG TAAAATGCAA
4801  ACCTTTCTGC TGCGATAGCA TTAGGCAGAG GTTTCTCACC ACGCTGGAGC
4851  AGCTTGGGTT AGAATCAAAG CGTGTTGATC TCTTGCCTTT GATTCTTTTC
4901  AATCACGACC ATATGCAAGC CTATTCCTTG ATGGATATTA GGTAAGATTT
4951  GACACATAGT GCTCTGTAAA ACACCGAGGC TTATAGATTC ACATATTTAA
5001  TTTACATTTA TTGCAGTTTG GACACATTCC CTTATGCTGG AACTACCACT
5051  ACCTGTGAGT CTCTCTACAT GGGAGTTCCA TGTGTTACAA TGGCTGGCTC
5101  AGTACATGCT CATAATGTTG GTGTCAGTCT TCTCACTAAA GTTGGTAAGC
5151  TCTTAGCAAA ATTTTTTTTT TTTTTTTGC  AAAAATTGTT GTTAGTCGAC
5201  ATCTTTTAGC TAATTCAGCC ATTTCTTGAT TCAGGATTAG GACACCTGGT
```

FIGURE 4C

```
5251  TGCCAAAAAT GAGGATGAGT ATGTTCAGCT ATCTGTTGAT CTAGCCTCTG
5301  ATGTCACAGC TCTTTCTAAA TTGAGAATGA GTCTCCGGGA TCTAATGGCT
5351  GGATCTCCTG TTTGTAATGG TCCTTCCTTT GCTGTTGGTC TTGAATCCGC
5401  ATATCGGAAT ATGTGGAAAA AGTACTGCAA AGGTGAAGTG CCGTCCTTAA
5451  GGCGAATGGA AATGCTGCAA AAAGAGGTCC ATGATGATCC CTTAATCTCA
5501  AAAGACTTGG GACCATCAAG AGTCAGCGTT ACTGGAGAAG CCACTCCGTC
5551  TCTCAAGGCC AATGGTTCTG CTCCTGTACC TTCCTCTTTA CCAACCCAAT
5601  CCCCGCAGCT CTCAAAGAGA ATGGACTCCA CTAGCTAGAT AACCAGCAAA
5651  TCGAGCTGCT GCGAAATGCC GGCAGAGAGT CTTGACCCAT CTGGAAAAGG
5701  TGTGAAAGAA AGAGTCGATG AGCTTTTCCT GCTATTTACT TCCAAGACAA
5751  TAGGAACTAG ACTTTAGATT ACTGCTTGTG TAGTAAAAAG AATAGTAAAA
5801  CCAGCTCTTT CTTTTGTTGT ATCTCTTTCT ACTCTTAGTT TAGCTTTACA
5851  TGATTCTTGG GAAGTCGTTA GGTGGTAGTG GATTTGGAGT TTTTCTTCTC
5901  ATTTGAGAGA TCAAGTTGTT GTGTATCGAT TAGGGTTTTA AGGCTTTTTA
5951  GGATGTTTTC ATGTGTTGGA TTTTGACTCA TATGATAGTA AATATAGTTA
6001  TAGAAAGCTT TTCGGTGCCT TTACCTATTT CATAATATAA TTATCTAAAA
6051  CTCCTGCTTA AGCTTAATCC CATAGGTGAG ACCCAATGAA AGACTTTTGA
6101  CTTGTATGAT TATGTTGCCA ACTCCATATC TCTCTTTAAT TAATTAATAT
6151  GGAGAGAGTA AAAAGGCAAG CAACTAACTA CTCTTCAATT CAACACTTCT
6201  TCTGCTCCAT TGCTTCCACC AGAACCCTAA AGACCTTATA AAACCCAATC
6251  CCAAATCCCT TTGCTCATTC ACCACCAAAG CATCCAACTT TCTTTGCTTC
6301  CTCTTTCAAA GCAACACAAA ATATTAAATC TCAAGAAACA AAGTAAAGAA
6351  AAATGAAGAA CGAATCTACC TTCATTGATG TCCCTGCAGA ATCCAGCTCA
6401  GCCATGAAAG GCAAAGCTCC TCTAATCGGT GTAGCAAGAG ACCACACTAC
6451  TAGTGGCTCA GGTGGAT
```

FIGURE 5

BLAST Alignment of SPY Protein and Translation of Maize cDNA

```
SPY Prot¹:   609  DSLADPPDTKQKQVEELVRLPDCFLCYTPSPEAGPVCPTPALSNGFVTFGSFNNLAKITPKVLQVWARILCAVPNSR  685
Consensus         DSL DPP TKQK VEELVRLP+ FLCYTPSPEAGPVCPTPA+SNGFVTFGSFNNLAKITPKVLQVWARILC+VPNSR
Maize²:        2  DSLTDPPMTKQKHVEELVRLPESFLCYTPSPEAGPVCPTPAISNGFVTFGSFNNLAKITPKVLQVWARILCSVPNSR  232

Score = 379 (174.0 bits), Expect = 7.5e-52, Sum P(2) = 7.5e-52
Identities = 70/77 (90%), Positives = 73/77 (94%), Frame = +2
```

¹Numbers indicate the first and last amino acid residues SPY protein region in the alignment.
²Numbers indicate the first and last nucleotide residue of the maize cDNA translated for the alignment.

Expected T-DNA Structure

Structure of T-DNA Insert in SPY

SacI Plasmid Rescue Product

ARABIDOPSIS SPINDLY GENE, METHODS OF IDENTIFICATION AND USE

FIELD OF THE INVENTION

This invention relates to the regulation of plant growth and to the identification and use of a gene affecting the response to gibberellins.

BACKGROUND OF THE INVENTION

This invention was made with government support under grants GM40553, GM07323, and GM15964 awarded by the National Institutes of Health and IBN-9317524 awarded by the National Science Foundation. The government has certain rights in the invention.

Gibberellins (GAs) are a major class of plant hormones controlling many developmental processes including seed development and germination, flower and fruit development, and flowering time. Gibberellins (GAs) play a role in a number of growth and developmental processes in plants. Severe GA-deficient mutants may exhibit reduced seed germination, dwarfism of virtually all organs, and aberrant flower, fruit and seed development. Although the GA biosynthetic pathway has been studied for some time little is known about GA perception or signal transduction.

Genetic analysis has uncovered two classes of mutants which are affected in their response to gibberellins. One class consists of dominant or semi-dominant mutants resembling gibberellin-deficient mutants but exhibiting reduced or no sensitivity to gibberellin. Mutants of this type have been isolated in maize, wheat and *Arabidopsis thaliana* (arabidopsis).

The second group, the "slender" mutants, have a recessive over-growth phenotype that is phenocopied by repeated treatments of wild type plants with gibberellin, and is consistent with a defect causing constitutive gibberellin response. These mutants have been studied in pea, tomato, barley and arabidopsis (Jacobsen, S. E. & Olszewski, N. E. (1993) *The Plant Cell* 5:887–896). Slender mutants in pea, tomato and barley contain lower endogenous levels of gibberellins than wild-type plants.

A slender phenotypic mutation in arabidopsis is termed the "spindly" or "spy" mutation. The spindly mutation is characterized by elongated petioles, yellow-green leaves, early flowering, long spindly bolts, partial male sterility and parthenocarpic fruit development. These phenotypes are also observed in wild type plants exhibiting a gibberellin overdose syndrome due to external applications of gibberellin (Jacobsen, et al. supra).

Spy phenotypic mutants were isolated from $M_2$ populations of ethyl methylsulfonate (EMS)-mutagenized wild-type seeds by selection for germination in the presence of the gibberellin biosynthesis inhibitor, paclobutrazol (Jacobsen, et al. supra). The phenotypes of the plants were typical of spy mutants and all of these phenotypes are observed, at some level, in wild type plants which have been repeatedly sprayed with $GA_3$.

Growth retardants, typically in the form of sprays or washes are widely used, particularly in greenhouses to control plant growth. These chemicals act by reducing gibberellin levels of the plant. Direct treatment of plants with gibberellins or their analogs increase plant size over the entire treated area of the plant. While spindly and slender phenotypes have been described as early as 1922, the gene or genes associated with these phenotypes remain ellusive. Identification of the gene or genes associated with these phenotypes would permit gibberellin expression to be controlled without the need for chemical treatment. This will reduce chemical usage and minimize a potential environmental hazard.

SUMMARY OF THE INVENTION

This invention relates to the identification and use of a novel gene controlling plant growth and development by affecting responses to gibberellins.

In one aspect of this invention an isolated nucleic acid fragment is claimed that comprises at least nucleic acids 2175–2405 of SEQ ID NO:1. The invention contemplates a vector comprising a promoter and a nucleic acid fragment comprising at least nucleic acids 2175–2405 of SEQ ID NO:1, cells containing the vector and transgenic plants expressing protein encoded by an exogenously derived nucleic acid fragment comprising at least nucleic acids 2175–2405 of SEQ ID NO:1 as well as transgenic plants encoding an exogenously-derived nucleic acid fragment comprising at least nucleic acids 2175–2405 of SEQ ID NO:1 and a transgenic plant expressing a polypeptide encoded by an exogenously-derived nucleic acid fragment comprising at least amino acids 609–685 of SEQ ID NO:2. In a preferred embodiment the promoter is plant tissue specific and plant tissue specific vectors include promoters specific for fruit expression and for green-tissue expression.

In another embodiment of the invention a transgenic plant is claimed that expresses a polypeptide where the polypeptide is encoded by an exogenously-derived nucleic acid fragment capable of hybridizing under highly stringent hybridization conditions to an isolated nucleic acid fragment comprising at least nucleic acids 2175–2405 of SEQ ID NO:1.

In another embodiment of the invention an isolated nucleic acid fragment is contemplated that contains the tetratricopeptide repeat region and comprises nucleic acids 579–1640 of SEQ ID NO:1. Vectors comprising a promoter and the tetratricopeptide containing region (nucleic acids 579–1640 of SEQ ID NO:1) are also contemplated along with cells containing the vector and transgenic plants expressing protein encoded by an exogenously-derived nucleic acid fragment comprising at least nucleic acids 579–1640 of SEQ ID NO:1. Isolated nucleic acid encoding the polypeptide of SEQ ID NO:2 is also a part of this invention. The term exogenously-derived refers herein to nucleic acid fragments introduced into a plant that may or may not now be incorporated into the plant genome through methods of transformation that are known in the art. For example, a nucleic acid fragment is exogenously-derived if it was incorporated into a vector and is introduced into a plant irrespective of whether or not the plant contains an endogenous (its own) copy of the nucleic acid fragment.

In another aspect of this invention a method is disclosed for identifying a gene from a plant comprising the steps of identifying at least a first clone from a cDNA library from a plant that hybridizes under low stringency hybridization conditions to a probe comprising nucleic acids 2175 to 2405 of SEQ ID NO:1, wherein the clone contains at least a portion of an open reading encoding a polypeptide with a C-terminus having at least 50% amino acid homology to amino acids 609–685 of SEQ ID NO:2, obtaining a full-length clone, wherein the full-length clone has about 100% nucleic acid homology to the open reading frame of said first clone and determining if the full length clone contains at least one tetratricopeptide repeat region. The determining step additionally may comprise determining if the tetratricopeptide repeat region of the full-length clone hybridizes under stringent hybridization conditions to a nucleic acid fragment consisting of nucleotides 579–1640 of SEQ ID NO:1.

The invention also relates to an isolated recombinant gene selected by the method of identifying at least a first clone from a cDNA library from a plant that hybridizes under low stringency hybridization conditions to a probe comprising nucleic acids 2175–2405 of SEQ ID NO:1, wherein the clone contains at least a portion of an open reading frame encoding a polypeptide with a C-terminus having at least 30% amino acid homology to amino acids 609–685 of SEQ ID NO:2, obtaining a full-length clone, wherein the full-length clone has about 100% nucleic acid homology to the open reading frame of the first clone and determining if the full length clone contains at least one tetratricopeptide repeat region. Preferably the open reading frame of the gene has at least a 70% homology to SEQ ID NO:1.

An isolated gene from a plant is disclosed where the gene encodes a polypeptide where a portion of the polypeptide has a 30% amino acid homology to amino acids 609–685 of SEQ ID NO:2, wherein the polypeptide encoded by the gene includes a tetratricopeptide repeat region and wherein introduction of a vector directing expression of the gene into a plant produces a transgenic plant with a spindly phenotype.

The invention also relates to a method for identifying a gene from a plant comprising the steps of searching a gene database for a nucleic acid sequence encoding a polypeptide from a plant and having at least 30% amino acid homology to the amino acid fragment corresponding to amino acids 609–685 of SEQ ID NO:2 and determining whether the open reading frame includes a tetratricopeptide repeat region.

The following definitions are employed throughout this disclosure.

In eukaryotes, RNA polymerase II catalyzes the transcription of a structural gene to produce mRNA. A DNA molecule can be designed to contain an RNA polylmerase II template in which the RNA transcript has a sequence that is complementary to that of a specific mRNA. The RNA transcript is termed an antisense RNA and a DNA sequence that encodes the antisense RNA is termed an antisense gene. Antisense RNA molecules are capable of binding to mRNA molecules, resulting in an inhibition of mRNA translation.

The term cDNA library refers to a collection of nucleic acid fragments originally derived from reverse transcription of isolated mRNA. The cDNA library contains a variety of different clones with different sequences. The individual cDNA sequences may or may not contain open reading frames and they may or may correspond to a full length mRNA transcipt.

A sibling plant refers to plants derived from seeds having a common parent.

The tetratricopeptide repeat region of this invention refers to amino acids 77–430 of SEQ ID NO:2 and to sequences having tetratricopeptide structural domains as enumerated in this disclosure.

An expression vector is a DNA molecule comprising a gene that is expressed in a host cell. Typically, gene expression is placed under the control of certain regulatory elements, including constitutive or inducible promoters, tissue-specific regulatory elements and enhancers. Such a gene is said to be "operably linked to" the regulatory elements A cloning vector is a DNA molecule, such as a plasmid, cosmid or bacteriophage that has the capability of replicating autonomously in a host cell. Cloning vectors typically contain one or a small number of restriction endonuclease recognition sites at which foreign DNA sequences can be inserted in a determinable fashion without loss of an essential biological function of the vector, as well as a marker gene that is suitable for use in the identification and selection of cells transformed with the cloning vector. Marker genes typically include genes that provide antibiotic resistance.

Exogenous denotes some item that is foreign to its surroundings and particularly applies to a class of genetic contructs that is not found in the normal genetic complement of the host plant. The term "clone" refers to the exogenous insert that has been inserted into the cloning vector, here a SPY gene or a portion thereof.

Heterologous is a noun modifier indicating a source that is different. For example, a heterologous promoter used with a structural gene of the present invention is a promoter that is different from that of the structural gene.

An isolated recombinant nucleic acid fragment refers to RNA or DNA that is not originally from the genomic DNA of the particular organism into which it is introduced. The isolated fragment can be used as a probe, incorporated into an expression vector or otherwise used in a variety of molecular biology methods.

Two nucleic acid molecules are considered to have a substantial sequence similarity if their nucleotide sequences share a similarity of at least 50% and protein encoded by the nucleotide sequences have a homology of at least 30%. Sequence similarity determinations can be performed using the FASTA program (Genetics Computer Group Madison, Wis.). Alternatively, sequence similarity determinations can be performed using BLASTP (Basic Local Alignment Search Tool) of the Experimental GENINFO Blast Network Service. See also Pasternak, et al. *Methods in Plant Molecular Biology and Biotechnology*, Glick, et al. (eds.), pages 251–267 ( Press, 1993).

Stringent hybridization conditions are understood in this disclosure as those nucleic acid hybridization conditions normally used by one of skill in the art to establish at least a 90% homology between complementary pieces of DNA or between DNA and RNA. In this disclosure 90% homology is preferred for hybridization of the C-terminus fragment in screening strategies to identify other SPY genes. Lesser homologies using lower stringency conditions may be desired such as at least 50% homology or preferably at least 80% homology.

A suitable promoter is a promoter that controls gene expression in cells that are to be altered developmentally by the manipulation of genes controlling response to gibberellin.

A transgenic plant is plant having one or more plant cells that contain an expression vector.

BRIEF DESCRIPTION OF THE FIGURES

FIG. 2 is the deduced amino acid sequence of the SPY protein (SEQ ID NO:2). The protein is shown in three blocks, the N-terminus (residues 1–76), the 10 tetratricopeptide repeats (TPRs, residues 77–430) aligned with each other, and the C-terminus (residues 431–914). Below the TPR alignment is a consensus sequence: amino acids are shown if present in at least 5 of the SPY TPRs. Residues indicated with a double underline have the following alterations in the mutant alleles: $Met^{354}$ to $Gln^{376}$ are absent in spy-1 and spy-2, $Gly^{593}$ is converted to Ser in spy-3, and $Cys^{845}$ is converted to Tyr in spy-5. Abbreviations for the amino acid residues are A, Ala; C, Cys; D, Asp; E, Glu; F, Phe; G, Gly; H, His; I, Ile; K, Lys; L, Leu; M, Met; N, Asn; P, Pro; Q, Gln; R, Arg; S, Ser; T, Thr; V, Val; W, Trp; and Y, Tyr.

FIG. 3(A–C) is the sequence of the SPY cDNA (SEQ ID NO:1). The start codon for translation (ATG) and the stop codon (TAG) are indicated by the double underline. The single underline indicates the region deleted in mRNA of spy-1 and spy-2. Nucleotides mutated in spy-1, spy-3 and spy-5 are indicated in bold and the nucleotide of the mutant is indicated below.

FIG. 4(A–C) is a sequence of the SPY genomic region (SEQ ID NO:3). The bold G and C which are also underlined correspond to the first and last nucleotides of the SPY cDNA.

FIG. 5 is a Blast Alignment of the SPY protein sequences with a translation of a maize cDNA. A BLAST alignment of a portion of the SPY protein (SPY Prot) and a translation of a maize cDNA (Maize). The consensus of this alignment are indicated between the SPY and maize sequences (consensus). The statistics provided by the BLAST program are included below the alignment.

FIG. 6(A–C) provides the maps of 3850:1003 T-DNA, as the T-DNA existed in spy-4 plants and the plasmid rescued from spy-4.

DETAILED DESCRIPTION OF THE PREFERRED EMBODIMENTS

Figure 1:
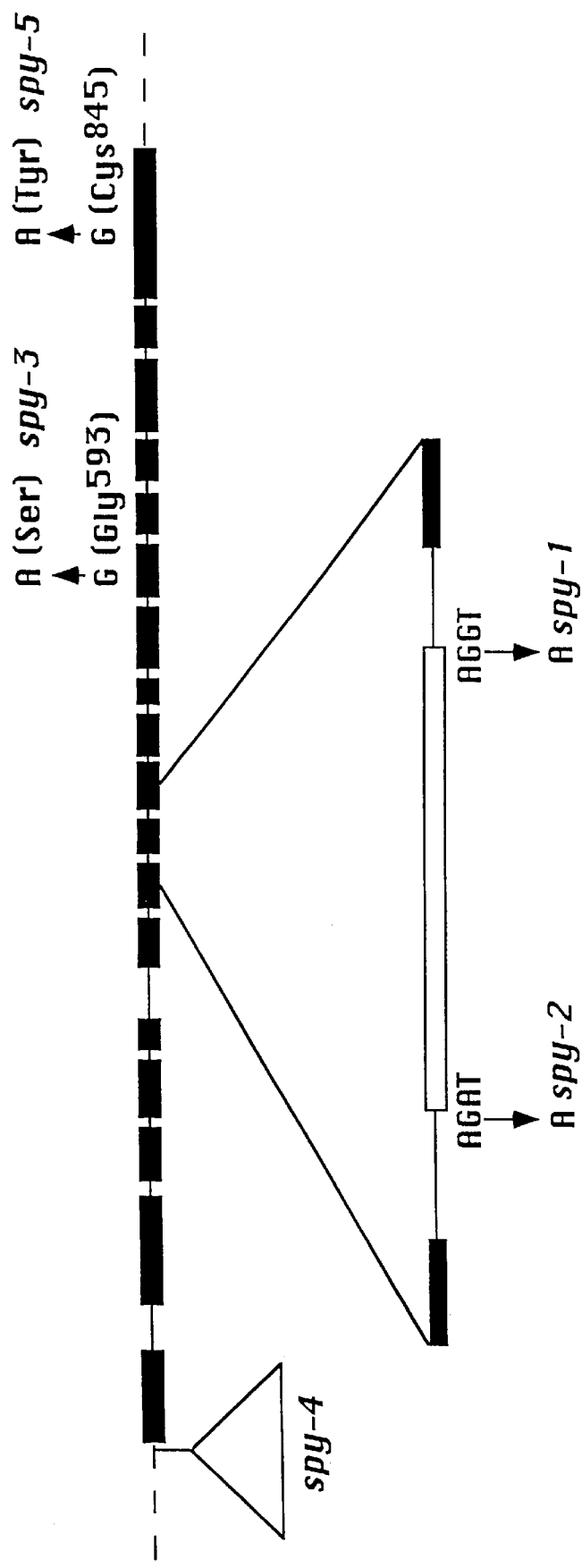
FIG. 1 is a schematic detailing the structure of the SPY gene and spy mutations. Broken lines represent the region outside the 3.5 kbp cDNA. Unbroken lines represent introns. Solid bars represent exons. Introns and exons were identified in the genomic sequence by comparing the sequence of the genomic clone with that of the cDNA. The open bar represents the exon that is skipped in spy-1 and spy-2. Arrows indicate mutated nucleic acid residues. The triangle represents the T-DNA insertion.

The identification of the genes involved in gibberellin signal transduction and regulation have a number of commercial applications. For example, overproduction of gibberellin results in increased plant growth while underproduction of gibberellin reduces plant growth. Control of gibberellin levels provides a mechanism for controlling plant development including plant height, fruit growth, flower development, leaf size, and the like. In maize, higher levels of GA result in increased vigor in hybrid maize (Rood, et al. (1988) *Science* 241:1216–1218).

The present invention discloses the identification and use of a gene that is involved in gibberellin signal transduction. Inactivation of the gene produces a spindly phenotype and introduction of the gene into plants rescues the spindly phenotype. Methods are disclosed for isolating the gene in a variety of plant types and using the gene to effect changes in the level of gibberellin expression.

Slender mutations in plants have a number of similar phenotypic characteristics. In arabidopsis, the slender mutant phenotypes are characterized as producing plants that are physically similar to plants that are repeatedly treated with gibberellins. Although slender phenotypes have been identified, the relationship of the phenotype to one or more genes has not been understood. In previous studies a plant growth regulator, paclobutrazol, was used to identify mutants with altered gibberellin synthesis pathways. Paclobutrazol inhibits the monooxygenases involved in the oxidation of ent-kaurene to ent-kaurenoic acid and reduces the plant's ability to synthesize active gibberellins.

Three spy mutants were identified that demonstrated resistance to paclobutrazol treatment (Jacobsen, S. E., et al. (1993) *The Plant Cell* 5:887–896). The gene or genes conferring the phenotype could not be predicted because the location of the gene was not known.

To identify the location of the spindly (spy) mutant, a spy phenotypic mutant was identified by first isolating a mutant expressing the spy phenotype from a library of more than 4,000 Agrobacterium-mediated seed transformation lines of arabidopsis having T-DNA insertions positioned throughout the genome(Arabidopsis Biological Resource Center (stock number CS3115 Columbus, Ohio) and was originally produced by K. Feldman (*The Plant Journal* 1:71–82, 1991). The T-DNA library was produced by inoculating germinating seeds with Agrobacterium containing 3850:1003 T-DNA and selecting progeny that are kanamycin resistant. (Feldman supra)

The T-DNA insert includes an engineered plant selectable marker that confers resistance to kanamycin. A kanamycin resistance gene functions in *E. coli* and *Agrobacterium tumefaciens*. In addition the T-DNA includes two copies of pBR322 that contains genes conferring bacterial resistance to ampicilin and tetracycline. A detailed discussion of the T-DNA insert is provided in Feldman (supra) and will not be detailed here.

Seeds from the library were selected for their ability to germinate in the presence of paclobutrazol (Jacobsen, supra). Pool number CS2635 contained two paclobutrazol resistant seeds (spy-4) that yielded plants with a spy phenotype. Similar to the spy alleles (Jacobsen, supra), spy-4 flowered earlier than wild type and displayed pale green foliage, partial male sterility and parthenocarpic fruit development. Other phenotypic details of spy-4 are provided in Example 1.

To determine whether or not the spy phenotype is produced from one or more genes, spy-4 was back crossed to a progenitor Ws plant. Of 107 F2 seedlings grown on 1X MS plates (Sigma Chemical, St. Louis, Mo.) supplemented with 1% (w/v) sucrose in 1% (w/v) agar containing 50 μg/ml kanamycin (kan). 80 of the seedlings were kan resistant. This suggested the presence of a single kan locus. Of 43 paclobutrazol resistant seedlings in the $F_2$ population, all were kan resistant. In contrast, only two thirds of the non-paclobutrazol resistant seedlings were kan resistant indicating a linkage between kan resistance and paclobutrazol resistance. In addition, seeds produced by crossing spy-4 and spy-1 plants germinated in the presence of paclobutrazol, the resulting F1 plants exhibited a spy phenotype indicating that spy-1 and spy-4 were allelic.

Segregation of the T-DNA kan resistance marker and spy-4 in backcrosses is consistent with the conclusion that spy-4 plants contain a single functional kan resistance locus that is linked to spy-4.

Although kanamycin resistance segregates as expected for a single Mendelian locus, it was still quite possible that spy-4 contained multiple linked T-DNA inserts or additional T-DNA inserts in which the KanR gene was either mutated or not expressed due to position effects.

Plasmid rescue was used to isolate plant DNA flanking the T-DNA insertion site after a genetic linkage was demonstrated between the kanamycin resistance locus resident in T-DNA and the spy-4 phenotype. The standard T-DNA plasmid rescue procedure involves the identification of restriction endonucleases that digest the T-DNA and regions flanking it such that the products of the reaction contain some DNA fragments that contain an intact Arabidopsis DNA flanking the T-DNA, bacterial origin of replication and a selectable marker for use in bacteria (Olszewski, N. E., et al. (1988) *Nucleic Acids Research* 16:10765). The products of this reaction are then ligated with T4 DNA ligase to produce monomer circles. The products of this ligation are introduced into *E. coli* and cells receiving the ligation product containing the T-DNA sequences and flanking Arabidopsis sequences are selected by virtue of their resistance to an antibiotic.

Standard plasmid rescue procedures could not be used in this instance because the T-DNA mutant had undergone mutations in the T-DNA insertions and the plasmids could not be rescued by standard methods known in the art. Because of the mutations in the inserts positioned near or in the spindly gene, there were no predictable protocols for rescuing the gene. These problems and the methods for identifying the gene are discussed in detail in Example 2.

Comparison between the sequence of the cDNA and the corresponding genomic region indicated that the spy mRNA is composed of 18 exons which have the potential to encode a 914 amino acid protein (see FIGS. 1 and 2). Nucleotides 351–579 encode the unique N terminus (res. 1–76) and nucleotides 580–1637 encode the TPR domain (res. 77–430). This region contained 10 copies of the TPR repeat. Nucleotides 1638–3091 encode the unique C-terminus (res. 431–914). The region from 1638–3091 did not include the TPR region and based on a search in sequence databanks is specific for SPY sequences. The SPY amino acid sequence was determined from the nucleic acid sequence identified from the isolated clone. The amino acid sequence was used to search protein databases for similar sequences. No close matches were identified.

As noted above, the SPY gene contains a tetratricopeptide repeat (TPR). In SPY, this repeat was identified as a 34 amino acid repeated sequence motif that has been found in a few other proteins (Sikorski, R. S., et al. (1991) *Cold Spring Harbor Symposia on Quantitative Biology* LVI:663–673 and Lamb, J. R., et al.(1995) *TIBS* 20:257–259). FIG. 2 shows an alignment of the 10 TPR repeats found in the N-terminus of the predicted SPY protein and a consensus sequence for the 10 repeats.

SPY cDNAs from the paclobutrazol-induced phenotypic mutants, spy-1, 2, 3 (Jacobsen, supra) and spy-5, another phenotypic mutant (Wilson, et al.(1995) *Plant Phys.* 108:495–502) were sequenced to confirm that the isolated sequence yielded the RNA sequence encoding the SPY protein. Each allele contained a mutation. The spy-3 (G at 2127 is mutated to an A) and spy-5 mutations (G at 2884 is mutated to an A) caused amino acid substitutions in the C-terminus of the protein.

A shorter PCR product was obtained from spy-1 and spy-2 RNA than from wild-type RNA. The eighth exon was missing in the RNAs from spy-1 and spy-2 plants. Reverse transcriptase followed by polymerase chain reaction (RT-PCR) was used to amplify the region containing the 8th exon to determine which portions of the exon was missing in the spy-1 and spy-2 mutants. Preferred methods for determining the sequences are provided in Example 2. Sequencing of the genomic DNA from these two lines showed that the spy-1 mutation affects the 5' exon-intron junction of the eighth exon, while spy-2 affects its 3' intron-exon junction. Both spy-1 and spy-2 plants lacked the eighth exon from residues 1410 to 1478 (FIGS. 1 and 2).

An analysis of the mutants indicated that the TPR regions are important for SPY protein function. Mutations in the spy-1 and spy-2 plants corresponded to a loss of 23 amino acids, including the last 9 amino acids of the eighth TPR and the first 14 amino acids of the ninth TPR. The spy-1 and spy-2 mutations caused the loss of the region from Met (354) to Gln (376). This indicated that TPR repeats were needed for wild type activity. The spy-3 and spy-5 mutations converted Gly(593) to Ser and Cys(845) to Tyr respectively. This indicated that the unique C-terminal region was also important. Analysis of the SPY sequence indicates that SPY proteins contain a TPR domain and a unique C-terminal region.

Final confirmation that the identified gene encoded SPY was provided by the observation that a cosmid clone containing the SPY gene (clone 2118) complemented the paclobutrazol germination defect of the spy-1 mutant (see Example 2). Southern blot analysis confirmed that SPY is a single copy gene. Using a restriction length fragment polymorphism present in a SPY containing cosmid clone, the SPY locus was mapped to the top of chromosome 3 in *Arabidopsis thaliana* between RFLP markers 1At243 and hsp70-9.

Based on several gene database searches (GenBank, EMBL, PIR and Swiss-Prot), it is evident that the SPY protein contains a unique N-terminus (res. 1–76 cDNA nucleotides 351–578, see SEQ ID NO:1), a unique TPR domain (res. 77–430, nucleotides 579–1640, see SEQ ID NO:1) containing 10 copies of the tetratricopeptide repeat, and a unique C terminus (res. 431–914, nucleotides 1641–3092, SEQ ID NO:1)

SPY is only the second TPR gene known in plants (Torres, J. H., et al. E. (1995) *Plant Mol. Biol.* 2:1221–1226). Other TPR-containing genes are known and there is a growing family of TPR proteins which perform diverse functions. Without intending to limit the scope or content of this invention in any way, among the proposed functions for TPR proteins are transcriptional repression, mitochondrial and peroxisomal protein transport, cell cycle regulation, protein kinase inhibition, and heat shock response (Sikorski, et al. supra, and Lamb, et al.(1995), supra).

There is little in common with the general function of these proteins, but they are often found in protein complexes and it has been proposed that the TPRs form amphipathic alpha-helices that mediate the protein-protein interactions. For CYC8, a yeast transcriptional repressor containing 10 TPRS, it was shown that the first three TPRs are necessary and sufficient for direct interaction with another non-TPR protein, TUP1 (Tzamarias and Struhl, 1995 *Genes Dev.* 9:821–831). The CYC8-TUP1 complex is thought to be recruited by specific DNA binding proteins and acts as a transcriptional repressor. Thus, without intending to limit the scope or content of this invention, it is likely that SPY acts to suppress GA signal transduction in part by interacting with other proteins through one or more of its TPR domains.

While there are no obvious sequence motifs in the 485 amino acid non-TPR carboxy-terminal region that might indicate a specific biochemical function, the spy-3 and spy-5 mutations demonstrate that this domain is important for normal SPY activity. Comparison of this region with protein database sequences reveals similarity with a predicted protein from *C. elegans*, K04G7.3 (Wilson, R. et al. (1994) *Nature* 368:32–38)) and less similarity with ESTs from the blood fluke *Schistosoma mansoni* (accession T14591 GenBank) and human (accession R76782 GenBank). The glycine affected in the spy-3 allele is conserved in K04G7.3, while the cysteine affected in spy-5 is not. Although the function of K04G7.3 is unknown, it also contains an N-terminal TPR region which exhibits the highest level of similarity to the SPY TPR domain. This suggests that SPY and K04G7.3 are members of a new class of regulatory molecules that is likely to be present throughout the eukaryotes.

The SPY gene of arabidopsis contains a novel C-terminal domain (cDNA nucleotides 1641–3092 of SEQ ID NO:1 and in particular amino acids 632–685 and the corresponding nucleotide residues 2238 to 2405) that is useful for identifying SPY genes in other plants. In a particularly preferred method of this invention probes from the C-terminus are used to screen a cDNA library. Example 4 provides a preferred strategy for library of maize sequence tags and a maize cDNA library (see Example 4). The results of this study identified the conserved C-terminus in maize. FIG. 5 provides a sequence comparison between a portion of the C-terminus of arabidopsis and maize. A particularly preferred region of the C-terminus for use as a probe is the region between amino acids 609 to 685 of SEQ ID NO:2 corresponding to nucleic acids 2175–2405 of SEQ ID NO:1 and another preferred region includes the region extending from 631 to 685 of SEQ ID NO:2 that corresponds to nucleic acids 2244–2405 of SEQ ID NO:1. Hybridization studies using the C-terminus as a probe of southern blots of genomic DNA from turnip and rice also indicate the presence of a single SPY gene.

Gibberellins are important in corn development. There is a correlation between increased vigor in hybrid maize and higher gibberellin levels compared to parental levels, and the greater response of inbreds (compared to hybrids) to exogenously applied gibberellin. The gibberellin biosynthetic loci appears to be a quantitative trait loci for height in maize hybrids. The importance of gibberellins in plant development is further evidenced in the phenotype of gibberellin-deficient mutants of maize, which includes: reduced plant stature, due to shorter internode lengths; shorter broader leaves; less branching of the tassels; and the development of anthers on the normally spitillate ear resulting in perfect flowers (Emerson, et al. (1922) *Genetics* 7:203–227). Gibberellins affect the development of pistils and stamens in maize by arresting development of the stamens in both florets of the ear. This results in a staminate flower in the proximal floret and a mature perfect flower in the distal floret. The development of pistils and stamens in the tassel of gibberellin deficient mutants is delayed, but otherwise is unaffected.

Example 2 discusses the introduction of the Arabidopsis SPY gene into a spy phenotypic mutant to partially correct the effect of the endogenous mutated spy gene. Growth retardants are widely used, particularly in greenhouses to control, typically reduce, plant growth. Since these chemicals act by reducing gibberellin levels of the plant it should be possible to create plants with increased SPY protein levels that do not require chemical treatment. This will reduce chemical usage and minimize a potential environmental hazard. SPY offers an additional advantage in that it is likely to act only in the tissues/organs where its expression is altered thereby offering greater control than can be afforded using growth retardants that act systemically.

Genes or portions of genes are identified using searches of gene databases or by hybridization studies as disclosed in Example 4. Related sequences can be identified by hybridization at high stringency (conditions that allow sequences with/ that 90% identity to anneal) or lower stringencies (80 or 70% identify) Since the TPR repeats are not highly identical and TPR repeats of SPY genes are expected to be more similar to each other than to TPR regions of non-SPY genes, hybridizations with this regions can be used to identify SPY genes. Sequence homologies in gene database searches for genes with TPR homologies are considered signicant if the protein homology is at least 50%. If the TPR region is employed for database searching or hybridization studies, the presence of the non-TPR regions must be confirmed by hybridization or DNA sequencing. Sequence homologies in gene database searches for genes with homology to the C-terminus or a portion thereof are considered significant if the protein sequence has a 30% homology.

The SPY gene from a variety of plants can be incorporated into a variety of plant expression vectors to produce phenotypic modifications. Methods for incorporating the SPY gene into a suitable expression vector and the introduction of the vector into either monocots or dicots are well known in the art. Methods for transforming plant cells include microinjection, electroporation, Agrobacterium mediated transformation, direct gene transfer and particle bombardment such as using devices available from Agracetus, Inc. Madison Wis., and the like. Moreover preferred methods for introducing exogenous genes into plant cells and the production of transgenic plants is well known for a variety of plants. PCT Publication No. WO 94/28141 to Lange, et al. references many publications that disclose methods for transforming a variety of plant tissues.

Plants that have reduced levels of active SPY protein are taller than normal plants. Results provided by data disclosed here suggests that when SPY protein levels are increased by introducing extra copies of the SPY gene into plants, the plants have reduced stature and these methods and the gene can be used to modulate plant stature as well as early and late flower maturity. Development of semi-dwarf varieties of many crops (wheat) have been very important and have greatly enhanced yield. Treatment with gibberellins are used to enhance growth (grapes). In some cases it may be possible to create varieties of grapes with altered SPY protein levels that do not require treatment with gibberellins.

Inhibition of SPY expression can be used to mimic the effects of gibberellin overexpression in plants. In a preferred method for underexpression, antisense cloning methods are used. Antisense cloning has been demonstrated to be effective in plant systems and can be readily adapted by one of ordinary skill in the art using the SPY gene using published methods for antisense cloning of other genes (Oeller et al., (1991) *Science* 254:437–439,).

In general antisense cloning entails the generation of an expression vector encoding an RNA complementary (antisense) to the RNA encoding the SPY gene. By expressing the antisense RNA in a cell expressing the sense strand, hybridization between the two RNA species will occur resulting in the blocking of translation.

Gibberellins are involved in germination and exogenous applications of gibberellins can break seed dormancy. These observations suggest that manipulation of SPY levels may allow control of the process of germination. Overexpression of SPY may prevent germination but this inhibition may be overcome by treatment with gibberellins. This suggests that it is possible to develop strategies that allow propagation of elite varieties to be controlled by the producer of these varieties.

Antisense SPY or SPY-containing constructs can be used to shorten or lengthen the time to seed maturity of plants. Increased signal transduction shortens the time to flowering. Shortening the time to maturity is an advantage in some growth zones whereas increased time to maturity is an advantage in other growth zones.

The potential to specifically alter the growth of an organ or tissue is something that is not easily accomplished using conventional breeding or chemicals. Therefore, SPY opens avenues for improvement of plants that have not been pursued previously. Mutations in the SPY gene cause parthenocarpic (development without fertilization) fruit development. Therefore, plants engineered for under expression of SPY in flowers may produce seedless parthenocarpic fruit.

This invention also relates to tissue specific expression or repression of the SPY gene. The term tissue-specific expression refers to expression or inhibition of the SPY gene in a particular tissue. Tissue-preferential and tissue-specific promoters are used to effect tissue-specific expression meaning that the tissue-specific promoter is used to indicate that a given regulatory DNA sequence will promote transcription of an associated expressible DNA sequence entirely in one or more tissues of a plant, or in one type of tissue, while essentially no transcription of that associated coding DNA sequence will occur in all other tissues or types of tissues of the plant. Numerous promoters whose expression are known to vary in a tissue specific manner are known in the art. Once example is the maize phosphoenol pyruvate carboxylase promoter, which is green tissue-specific. Other green tissue-specific promoters include chlorophyll a/b binding protein promoters and RubisCo small subunit promoters. Pollen-specific promoters are available from plant calcium-dependent phosphate kinase gene.

The Example 4 and 5 disclose methods for incorporating SPY genes in other plants. Tissue specific constructs producing the antisense copy of the SPY RNA would reduce SPY protein levels producing more growth of the tissue, i.e. increased stature, while tissue specific constructs producing the SPY mRNA would cause an increase in SPY protein and hence less growth of the tissues, i.e. reduced stature in those tissues where the SPY gene was expressed. The tissue/organ specificity of the constructs could be controlled using promoters with appropriate properties to drive the expression of the constructs.

In addition to controlling growth, gibberellins also affect germination of seeds, time of flowering and response to stress. Therefore, by altering SPY levels as described above it may be possible to modify these processes as well. Seeds with reduced levels of SPY protein exhibit reduced dormancy and plants with reduced SPY protein flower earlier.

The present invention is illustrated in further detail in the following examples. These examples are included for explanatory purposes and should not be considered to limit the invention.

EXAMPLE 1

Description of the spy-4 allele

Although spy-4 had characteristics of other spy alleles, in addition, spy-4 exhibited obvious partial dominance with respect to flowering time. Under long day conditions, wild-type plants of the ecotype Wassilewskija (Ws) flowered after producing 9.4+/−0.5 rosette leaves, plants heterozygous for spy-4 flowered after producing 5.5+/−0.2 rosette leaves, and plants homozygous for spy-4 flowered after producing only 2.0+/−0.0 rosette leaves. Plants heterozygous for spy-4 did not exhibit partial sterility and seeds heterozygous for spy-4 failed to germinate in the presence of paclobutrazol, indicating that these traits are fully recessive. The homozygous flowering time phenotype suggests that spy-4 is the strongest of the spy alleles identified.

EXAMPLE 2

Isolation and Sequencing of SPY gene

The SPY gene was cloned with the aid of the T-DNA insert. The use of the T-DNA system for cloning is not predictably successful because the sequence incorporates randomly into the genome and there is no guarantee that any particular gene will contain an insert creating a recognizable mutant phenotype. Selection of a particular mutant phenotype does not guarantee that the mutant relates to a single gene. Moreover mutant phenotypes with reduced stature are rare in T-DNA libraries.

By hybridizing blots containing spy-4 DNA with subcloned portions of the 3850-1003 T-DNA, it was determined that the spy-4 plants contained a single partial T-DNA. When 28 F3 families each derived from F2 plants that were either wild-type or heterozygous for spy-4 were analyzed for the presence of pBR322 sequences, the pBR322 sequences cosegregated perfectly with spy-4. These results indicated that the T-DNA insert was responsible for the spy-4 allele and demonstrated that the T-DNA sequence was useful as a probe to clone SPY.

Figure 6A:
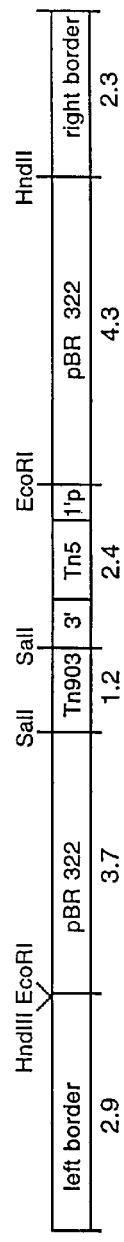
FIG. 6A illustrates the structure of the 3850:1003 T-DNA. Restriction sites are indicated above the map and the sizes of different segments of the T-DNA are indicated below the map.
Figure 6B:
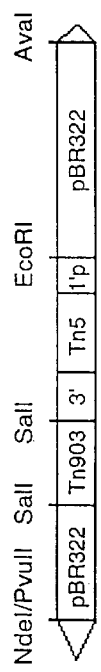
FIG. 6B indicates the highly deleted form of the T-DNA as it exists in the spy-4 genome.
Figure 6C:
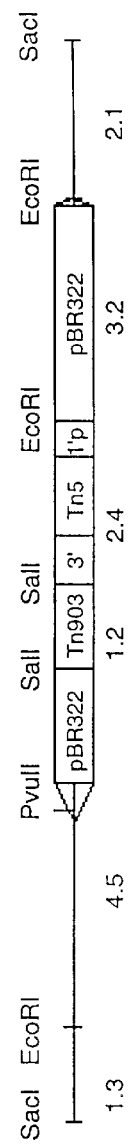
FIG. 6C indicates the structure of the construct obtained by plasmid rescue employing the restriction endonuclease SacI. The thin line on the left side of the T-DNA corresponds to the arabidopsis sequences used to probe genomic libraries constructed in pOCA18 to obtain the SPY gene. The probe extended from the SacI site at the left end of the map to the PvuII site near the junction between the arabidopsis and pBR322 sequences.

Because of alterations to the 3850:1003 T-DNA of the spy-4 genes, it was necessary to modify the standard cloning methods (Feldman, K. A. (1992) T-DNA insertion mutagenesis in Arabidopsis: Seed infection/transformation. In: Methods in Arabidopsis Research, C. Koncz, et al. World Scientific Publishing CO. Singapore pp. 274–289). A restriction map of the region containing the T-DNA and the surrounding DNA was produced. As shown in the map provided in FIG. 6A, T-DNA typically contains two pBR322 regions, a left border and a right border and working restriction endonuclease recognition sites distributed throughout the T-DNA. Analysis of the restriction map indicated that the ends of the T-DNA were deleted (FIG. 6B). The regions deleted included the left and right border sequences and a portion of each pBR322 sequence. In addition, non-T-DNA sequences from *Agrobacterium tumefaciens,* identified by DNA sequencing, were located adjacent to the right border side of the T-DNA. Detailed restriction mapping of the remaining portions of the two copies of pBR322 suggested that the copy normally adjacent to the right border might be functional but that the partial copy normally adjacent to the left border, which was located adjacent to arabidopsis sequences was not functional. Moreover, the ampicillin and kanamycin resistance markers appeared to be intact. The T-DNA sequences was analyzed and restriction enzymes that did not have recognition sites in the T-DNA were identified by trial and error. The enzymes tested included BclI, BglII, KpnI, NotI, SacI, SpeI and XbaT. In testing each of these enzymes in plasmid rescue, two enzymes appeared to work. These were BclI and SacI. The SacI derived plasmid was selected because it was larger (FIG. 6C).

Briefly, spy-4 genomic DNA was digested with each of these enzymes individually, the DNA in each reaction was then diluted to a concentration that favored circularization, rather than concatermerization, of the digested products and self-ligated using T4 DNA ligase. The resulting ligation product was introduced into *E.coli* (MC1061) by electroporation. Transformants were selected on medium containing kanamycin (25 µg/ml) and ampicillin (75 µg/ml). Samples from the BclI and SacI digestion yielded transformants. Restriction maps of plasmids isolated from these transformants were then generated and compared to the map of the genomic region to identify clones containing the T-DNA and flanking arabidopsis sequences. Plasmids from both the SacI and BclI rescue experiments had restriction maps consistent with them containing arabidopsis DNA sequences flanking the T-DNA causing the mutant phenotype. The SacI-derived plasmid was then used as a probe to obtain the wild-type SPY gene.

A 5.8 kb SalI to SacI fragment containing DNA and pBR322 that was derived from the SacI-rescued plasmid was subcloned into pbluescript II KS (Stratagene, La Jolla, Calif.). The resulting plasmid was digested with PvuII. This effectively separated the pBR322 sequences from the arabidopsis sequences but generated a restriction fragment in which the arabidopsis sequences were linked to the promoter for T7 RNA polymerase which is located directly adjacent to the cloning site in pBluescript II KS. The digestion products were transcribed by T7 RNA polymerase in the presence of $^{32}$P-UTP to generate a hybridization probe that was specific for arabidopsis sequences flanking the T-DNA insertion. This probe was purified and used to probe an arabidopsis genomic library constructed in the binary plant transformation vector pOCA18(Olszewski, (1988), supra). 30,000 colonies were grown and transferred to hybridization membranes and hybridized with the labeled RNA probe using standard methods for hybridization (Sambrook, et al. (1989) Molecular Cloning: A laboratory manual. Cold Spring Harbor Press). This screening identified six colonies containing plasmids that hybridized to the probe. The colonies were grown and the cosmids were isolated. Further analysis of two of these cosmids, 2118 and 4273 confirmed that they contained sequences that hybridized to the original probe and they were used in all subsequent experiments.

The EcoRI region from cosmid 4273 was labeled and used as a probe to probe a wild-type arabidopsis cDNA library. Clones were selected, sequences and compared to the plasmid rescue. A clone was selected that was closest to the T-DNA insert site. This clone contained a 3.5 kb fragment. The 5'-end of one 3.5 kb cDNA clone was found to be 13 bp downstream of the T-DNA insertion, and this cDNA was presumed to encode the SPY protein. Northern blot analysis indicated that RNA from wild-type and the four EMS alleles contain roughly similar amounts of a 3.5 kb transcript, which hybridized to this cDNA, but RNAs hybridizing to this cDNA were not detectable in spy-4 (not shown). This correlates with the observation that spy-4 is the strongest spy allele, and suggests that spy-4 may be an RNA null allele and that the 3.5 kb cDNA was a cDNA of SPY mRNA.

The 3.5 kb SPY cDNA was subcloned from lambda GT22A using polymerase chain reaction (PCR) followed by TA cloning (Invitrogen, San Diego, Calif., 92121). Three independent clones were sequenced using the Sequenase Version 2.0 DNA sequencing Kit (United States Biochemical Corporation; Cleveland, Ohio 44122). This sequence is designated SEQ ID NO:1. The protein encoded by this gene is designated SEQ ID NO:2. To sequence the spy alleles, reverse transcriptase PCR was performed on total RNA from the various alleles. The primers used for RT-PCR to generate cDNA were the same as those used to sequence the mutant alleles. Table 1 below provides the primers used in these experiments.

| Name | SEQ ID NO: | Sequence (5'–3') |
|---|---|---|
| JP67 | 4 | CTTCTCTTATGTCTACTCAA |
| JP48 | 5 | TGTTGAAGCTCACATTGGAA |
| JP66 | 6 | CACAGCTTTATCAAGGTT |
| JP50 | 7 | GGCCATAGCTCTGACA |
| JP72 | 8 | GAGAAATGCTAAAGTTCGACAT |
| JP64 | 9 | TACAGAGATGCTGGAA |
| JP62 | 10 | GCAGCAGAAAGGTTTGCAT |
| JP63 | 11 | ATCCAAATACTACGGGTT |
| JP71 | 12 | CTTTCACACCTTTTCCAGAT |
| JP58 | 13 | GAGATCCAGCCATTAGAT |

RT-PCR products were amplified from a region of the SPY RNA containing the eighth exon for wild type and the spy mutant alleles. By size, the RT-PCR product was smaller in spy-1 and spy-2 than in the wild type. RT-PCR products of the two alleles spy-1 and spy-2 had lost the 8th exon indicating that they had been misspliced. RNA from the wild type ecotype Ws or from the spy mutants was subjected to RT-PCR. Products were digested with HindIII, subjected to agarose gel electrophoresis, stained with ethidium bromide and visualized using UV light. A shorter PCR product was obtained from spy-1 and spy-2 RNA than from wild-type RNA. The sizes of the products are consistent with that expected in both the wild type (416 bp) and the splicing mutants (347 bp).

To sequence wild-type genomic DNA, an 8 kilobase XbaI fragment was subcloned from cosmid 2118 into pBluescript KS$^+$ (Stratagene, La Jolla, Calif.), and all intron and exon sequences were determined (6467 base pairs). To sequence the intron/exon junctions in the spy-1 and spy-2 mutants, genomic DNA was subjected to PCR using two primers JP81 (SEQ ID NO:14) with sequence GCTTTCCACTT-TAATCCACAT and JP82 (SEQ ID NO:15) with sequence GAAGATGAGAAAACAGACCT. and the products were sequenced directly.

Successful cloning of the SPY gene was confirmed because northern blots of mutant message as compared to wild type message hybridized with wild type cDNA probes indicated that SPY expression was lacking in the spy-4 mutant. The mutant alleles were sequenced to demonstrate the presence of mutations in each allele. The SPY gene was transformed using methods described in Valvekens, D., et al.(1988) *PNAS (USA)* 85:5536. into the spy-1 mutant and the transgenic spy-1 mutant containing the SPY gene had a partial reversion in its mutant phenotype. The SPY gene contains 17 introns and encodes a 3.5 kb transcript. The deduced protein contains 914 amino acids and contains 10 TPR to demonstrate that the isolated gene produced the observed phenotypic trait.

EXAMPLE 3

Characterization of the SPY protein

The SPY cDNA (see SEQ ID NO:1) is cloned into an expression vector such as PMALC (New England Biolabs) and expressed in *E.coli*. The protein is purified using methods known in the art such as affinity chromatography on a maltose containing column and used for biochemical studies designed to test the function of the SPY protein. The antisera is prepared to peptides or purified spy protein. Western blotting and tissue printing (Cassab and Varner (1987) *J. Cell Biol* 105:2581–2588, 1987) are used to assess the size, abundance and distribution of the spy protein in the different plant organs. Immunolocalization studies are performed to localize SPY within the cell (Varagona, et al. 1991 *The Plant Cell* 3:105–113). These methods are also used to detect changes in protein expression during the transition from vegetative growth to mature plant.

During the course of the current study, it was discovered that the previously described spy-1 line (Jacobsen, supra) most likely also carries a linked mutation at the HY2 locus. This linkage was identified because the HY2 locus maps in the same approximate region as SPY. Similar to spy mutants, hy2 mutants are early flowering and have pale green foliage. However, hy2 mutants do not exhibit male sterility and do not germinate in the presence of paclobutrazol (Jacobsen, et al. supra). Genetic complementation tests indicated that spy-1 fails to complement hy2-1, while spy-4 and spy-5 fully complement hy2-1. Sequencing of the SPY CDNA from two hy2 alleles detected no mutations in the coding region, and RNA blot analysis indicated that there was no change in SPY RNA size or abundance in these lines. Finally, the spy-1 allele exhibits a long hypocotyl phenotype, characteristic of hy2 mutants, while the, spy-4 and spy-5 alleles do not; and spy-1 has a more severe early flowering phenotype than spy-2 even though the molecular lesions in these two mutants are very similar. Taken together and without intending to limit the scope of this invention, these results suggest that the spy-1 line carries mutations in both the SPY and HY2 genes, and that SPY and HY2 are separate but linked genes affecting partially overlapping aspects of growth and development. Because our original genetic analysis was performed using the spy-1 line, we sought to confirm these results with the stronger spy-4 allele.

Double mutants were constructed between spy-4 and mutants affected in either GA biosynthesis or GA response. Mutations at the GA1 locus, the gibberellin biosynthesis enzyme ent-kaurene synthetase A (Sun, T., et al.(1994) *Plant Cell* 6:1509–1518.), block GA biosynthesis early in the synthesis pathway (Barendse, G. W. M., et al.(1986). *Physiol. Plant.* 67:315–319 and Zeevaart, J. A. D. et al. (1992). In *Progress in Plant Growth Regulation,* eds. Karssen, C. M., van Loon, L. C., & Vreugdenhil, D. (Dordrecht: Kluwer Academic Publishers), pp.34–42.). The phenotypes of the strong gal-2 mutant include dwarfism, failure to germinate, male sterility, and incomplete petal development. These phenotypes were reversed by applied gibberellins (Koornneef M., et al. (1980). *Theor. Appl. Genet.* 58, 257–263).

As with the weaker spy-1 allele, spy-4 is largely but not completely epistatic to gal-2, spy-4, gal-2 double mutants do not require exogenous GA for seed germination, petal development, and male fertility; but spy-4 gal-2 double mutant plant height is less than that of spy-4 single mutants. We have also found that, similar to the spy-1 gal-2 mutant, the spy-4 gal-2 double mutant still responds to exogenous GA treatment with an increase in plant height (S. Jacobsen, unpublished observation). These results suggests that spy-4 plants activate a basal level of GA independent signal transduction, but that they still respond to changes in the levels of active GAs in the plant.

To test the relationship between spy mutants and the semi dominant GA insensitive (gai) mutant (Koornneef, M., et al.(1985). *Physiol. Plant.* 65:33–39), we constructed the spy-4, gai double mutant. Whereas a weak allele, spy-5, was only partially epistatic to gai spy-4 is completely epistatic to gai. This unambiguous epistasis allows these two genes to be ordered and suggests that GAI acts upstream of SPY.

In summary, the results from these double mutant analysis together with the spy phenotype suggest that the wild type SPY product acts as a negative regulator of a portion of the GA signal transduction pathway that is common to all GA responses and that is downstream of both GA biosynthesis and the step affected in the gai mutant.

EXAMPLE 4

Method and Identification of SPY gene in other plants

There are at least two methods for identifying the SPY gene in other plants and for obtaining this gene as a clone for future transgenic studies. In the first method the SPY protein sequence was used to search sequence databases such as GenBank, EMBL and PIR to identify sequences capable of encoding similar proteins. Although searches of the public databases did not identify any plant sequences, a search of a cDNA database at Pioneer Hi-Bred identified a partial cDNA sequence encoding a protein with 90% identity to a portion of the non-TPR region of the SPY protein. FIG. 5 provides the alignment of the identified sequence and the region of homology between the SPY gene and a gene in maize.

The second approach involves using the SPY cDNA as a hybridization probe to identify clones that hybridize to the probe under conditions of low (at least 70% identity), medium( at least 80%) identity or high (at least 90% identity) stringency. Hybridization of a labeled ClaI fragment spanning the region from nucleotide 1601 to 3382 of the SPY cDNA to genomic blots containing DNA from turnip, maize and rice that had been digested with various restriction enzymes under conditions of low stringency detected hybridizing fragments in all of these species. Once a clone is identified, standard molecular techniques are used to identify the entire sequence of the gene.

A low stringency hybridization is considered for these studies as a prehybridization in 0.5M $NaPO_4$ (pH 7.0), 7% SDS, 1% BSA at 55° C. for 2 hours, hybridization in the same solution at 55° C. for 45 hours, two washes for 15 min with 1×SSC, 0.1% SC, 0.1% SDS at room temperature followed by 2 washes for 15 min with 1×SSC, 0.1% SDS at 37° C., or its effective equivalent. A medium stringency hybridization is considered in this disclosure to be a prehybridization in 0.5M $NaPO_4$ (pH 7.0), 7% SDS, 1% BSA at 55° C. for 2 hours, hybridization with probe in the same solution at 55° C. for 45 hours, and 2 washes for 15 min each, with 5×SSC, 0.5% SDS at room temp., 2 washes 15 min. each with 1×SSC inn 0.5–1.0% SDS at 37° C. and one wash for 15 min with 0.1×SSC, 1.0% SDS at 37° C. A high stringency hybridization is considered to include a prehybridization in 0.5M $NaPO_4$ (pH 7.0), 7% SDS, 1% BSA at 65° C. for 2 hours, hybridization in the same solution at 65° C. for 45 hours and 2 washes for 15 min each in 5×SSC, 0.5% SDS at room temperature, 2 washes at 15 min. each with 1×SSC, 0.5–1.0% SDS at 37° C. and 3 washes for 15 min each with 0.1×SSC, 1.0% SDS at 65° C. Those skilled in the art will recognize that other salts and detergents could be used in other combinations to produce other formulations for low, medium and high stringency hybridization and wash conditions and the exact formulas provided here are not intended to detract from the spirit of the distinction between the various stringency hybridization conditions.

Once the genes are identified they are introduced into suitable vectors with the appropriate enhancers, promoters and the like to direct facilitate incorporation of the gene into the plant and to permit expression of the exogenously-derived gene in the plant cells and tissues.

For dicots the genes are preferably incorporated into Agrobacterium vectors under the direction of a suitable promoter and transgenic plants are created using techniques known in the art including, but not limited to the use of binary plant transformation vector pOCA 18 (Olszewski, et al. (1988) supra) using the methods of that reference or those of Czako, M et al. (1986) *Plant Mol. Biol.* 6:101–109 and Jones, et al.(1985) *EMBO J.* 4:2411–2418). These clones are mobilized into *A. tumefaciens* strain AGLL (Lazo, et al. 1991) by tri-parental mating (Olszewski, et al. 1988, supra) and the resulting *A. tumefaciens* strains are used to generate transgenic plants using the methods of Valvekens, et al. (1988, supra).

For monocots the genes are incorporated into a suitable vector under the control of a suitable promoter, known to those skilled in the art of monocot transformation. The vector is incorporated into the monocot using techniques known in the art, including, but not limited to those disclosed in PCT Publication number WO 91/02071 to Adams, et al., those of European Patent Application Publication No. 586 355 A2, or Wan, et al. (1994) *Plant Physiol* 104:37–48. Those skilled in the art will recognize that there are a variety of methods known to create transgenic dicots and monocots and that these methods do not detract from the scope or content of this invention.

Alternatively it is possible to search nucleic acid and protein databases directly such as PIR-Protein, SWISS-PROT, GenBank and EMBL database with the deduced SPY protein from residues 431–914 for similar protein sequences or nucleic acid sequences capable of encoding a protein containing a similar region (>30% identity). Types of sequences searched should include cDNA, genomic protein and expressed sequence tags (ESTs). Once a positive identification is made, the identified sequence is assessed for the presence or absence of TPRs. No plant genes were identified in these databases to date with the characteristics of the genes of this invention, however, as further information is added to the databases, these searches may prove useful to the identification of other SPY genes.

Using a BglII restriction length fragment polymorphism present in cosmid 4111, the SPY locus was mapped on the Landsberg erecta X Columbia mapping lines in the laboratory of Dr. Elliot Meyerowitz as described in (Chang, C., et al.(1988) *Proc. Natl. Acad. Sci. U.S.A.* 85:6856).

EXAMPLE 5

Overexpression constructs of SPY

Overexpression of the SPY protein or a portion of the SPY protein, such as the fragments disclosed throughout this document, can be achieved by either overexpressing the transcribed region of the SPY gene or by oberexpressing the protein coding region of the SPY cDNA. Overexpression employing the gene sequences can be accomplished by replacing the SPY promoter with a stronger promoter such as the 35S promoter of Cauliflower mosaic virus (CaMV) and introducing the resulting gene into plants. Briefly, the transcribed region can be cloned into a plant transformation vector such as pBI121 (Clonetech Laboratories, Palo Alto, Calif.) in place of the beta-glucuronidase coding region in the sense orientation relative to the 35S promoter. Since pBI121 is a binary transformation vector, this construct can be introduced into Agrobacterium. The resulting strain can then be used to transform dicot plants by a protocol appropriate to the species being transformed. These methods are well-known and the literature provides preferred transformation strategies for a wide variety of plant species.

For overexpression using the cDNA, the cDNA is cloned in the sense orientation in place of the beta-glucuronidase coding region of pBI121. In this construct, the SPY coding region is flanked by the 35S promoter, which drives expression in plants, and the downstream NOS terminator, which terminates transcription. Given the large number of introns in the SPY gene, which must be removed during the formation of the mature mRNA, overexpression of the SPY cDNA which lacks the introns is the preferred method of overexpression.

Antisense constructs will be produced by replacing the beta-glucuronidase coding region of pBI121 with the SPY cDNA in an inverted orientation relative to the CaMV 35S promoter. This will allow the CaMV 35S promoter to drive the expression of antisense SPY RNA and the NOS terminator to terminate the production of this transcript.

References cited in this disclosure are incorporated herein by reference to the extent that they supplement, explain, provide a background for or teach methodology, techniques or compositions employed herein. Although the invention has been described in the context of particular embodiments, it is intended that the scope of coverage of the patent not be limited to those particular embodiments, but be determine by reference to the submitted claims.

What is claimed is:

1. An isolated nucleic acid fragment comprising nucleic acids 2175–2405 of SEQ ID NO: 1.

2. A vector comprising a promoter and a nulcleic acid fragment, comprising nucleic acids 2175–2405 of SEQ ID NO:1.

3. Transgenic plants expressing protein encoded by an exogenously-derived nucleic acid fragment comprising nucleic acids 2175–2405 of SEQ ID NO:1.

4. A cell containing the vector of claim 2.

5. The vector of claim 2, wherein the promoter is plant tissue specific.

6. The vector of claim 2, wherein the promoter is specific for fruit expression.

7. The vector of claim 2, wherein the promoter is specific for green tissue expression.

8. A transgenic plant comprising an exogenously-derived nucleic acid fragment of nucleic acids 2175–2405 of SEQ ID NO:1.

9. A transgenic plant expressing a polypeptide encoded by an exogenously-derived nucleic acid fragment comprising amino acids 609–685 of SEQ ID NO:2.

10. A transgenic plant expressing a polypeptide, where the polypeptide is encoded by an exogeniously-derived nucleic acid fragment capable of hybridizing under highly stringent conditions to an isolated nucleic acid fragment comprising nucleic acids 2175–2405 of SEQ ID NO:1.

11. An isolated nucleic acid fragment comprising nucleic acids 579–1640 of SEQ ID NO:1.

12. A vector comprising a promoter and at nucleic acid fragment, comprising nucleic acids 579–1640 of SEQ ID NO:1.

13. Transoenic plants expressing protein encoded by an exogenously-derived nucleic acid fragment comprising nucleic acids 579–1640 of SEQ ID NO:1.

14. A cell containing the vector of claim 12.

15. An isolated nucleic acid fragment encoding the polypeptide of SEQ ID NO:2.

16. An isolated recombinant gene selected by the method of:

identifying at least a first clone under low stringency hybridization conditions to a probe comprising nucleic acids 1641–3092 of SEQ ID NO:1, wherein the clone comprises a portion of an open reading frame encoding a polypeptide with a C-terminus conprising amino acids 609–685 of SEQ ID NO:2;

obtaining a full-length clone, wherein the full-length clone has about 100% nucleic acid homology to the open reading frame of said first clone; and determining if the full length clone contains at least one tetratricopeptide repeat region.

17. The gene of claim 16, wherein the open reading flame of the gene comprises SEQ ID NO:1.

18. The gene of claim 16, wherein the open reading frame of the gene has a tetratricopeptide repeat region that hybridizes under low stringency hybridization conditions to a nucleic acid fragment consisting of 579–1640 of SEQ ID NO:1.

19. The gene of claim 17, wherein the open reading frame of the gene hybridizes under stringent hybridization conditions to a nucleic acid fragment consisting of nucleic acids 2175–2405 of SEQ ID NO:1.

20. The gene of claim 17, wherein introduction of a vector capable of directing expression of the gene into a wild-type plant results in a spindly phenotype.

21. An isolated gene from a plant encoding a polypeptide where a portion of the polypeptide comprises amino acids 609–685 of SEQ ID NO:2, wherein the polypeptide encoded by the gene includes a tetratricopeptide repeat region and wherein introduction of a vector directing expression of the gene into a plant produces a transgenic plant with a spindly phenotype.

22. A transgenic plant comprising an exogenously derived nucleic acid fragment comprising SEQ ID NO:1.

23. An isolated nucleic acid fragment comprising nucleotides 1641–3092 of SEQ ID NO:1.

* * * * *

UNITED STATES PATENT AND TRADEMARK OFFICE
CERTIFICATE OF CORRECTION

PATENT NO.   : 5,912,415
DATED        : June 15, 1999
INVENTOR(S)  : Olszewski et al.

It is certified that error appears in the above-identified patent and that said Letters Patent is hereby corrected as shown below:

Title page,
Item [56], References Cited, OTHER PUBLICATIONS, within the "Stewart B. Rood et. al.," citation delete "242" and insert therefor -- 241 --.

Column 3,
Line 52, after "may" and before "correspond" insert -- not --.

Column 37,
Line 12, before "acid" delete "nulcleic" and insert therefor -- nucleic --.
Line 32, after "encoded by an" delete "exogeniously-derived" and insert therefor -- exogenously-derived --.
Lines 33-34, after "highly stringent" insert -- hybridization --.
Line 38, before "nucleic acid" delete "at" and insert therefor -- a --.
Line 41, before "plants expressing protein" delete "Transoenic" and insert therefor -- Transgenic --.

Column 38,
Line 9, after "a first clone" insert -- from a cDNA library from a plant that hybridizes --.
Line 13, after "C-terminus" delete "conprising" and insert therefor -- comprising --.
Line 20, after "opening reading" delete "flame" and insert therefor -- frame --.

Signed and Sealed this

Thirty-first Day of December, 2002

JAMES E. ROGAN
*Director of the United States Patent and Trademark Office*

SEQUENCE LISTING (1) GENERAL INFORMATION:

(iii) NUMBER OF SEQUENCES: 15

(2) INFORMATION FOR SEQ ID NO:1:

(i) SEQUENCE CHARACTERISTICS:
        (A) LENGTH: 3476 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:1:

```
GGAGAGCTAA TCTGAGTCGT TGCCTCTGTC CACTGGCTCG GACCGACCTC GTACCTCTTT        60
CATTTGTCCT CGAGCTTATA ATAGAGGCTA CGCGTCGCCG CCACCTCCGC TCCATCCATT       120
CACGGCCAAG CGACGACTCC ACCGCTTAGG CTTGGCGTCT GAGGTATACT GATCAACGCT       180
TTCTGTTTTC GGAGGAGCGA GGCGAGATCA GCTTCTCTTA TGTCTACTCA AACATATCAT       240
TCTTCTTTAG CCACTCGATT TCTTCTCTAG CGGCTCCAGA GGTTTCGTCG CTACAGAGTC       300
AAGTTCCTCT TTTCAGGTTT TGTGGTGAAC AAGATTTTAG TTACAAAAAA ATGGTGGGAC       360
TGGAAGATGA TACTGAGAGA GAGAGGTCAC CAGTCGTAGA GAATGGTTTT TCCAATGGGT       420
CTCGGTCTTC TTCTTCTAGC GCAGGTGTTT TGTCTCCATC ACGAAAGGTC ACTCAGGGGA       480
ACGATACACT TTCTTATGCC AATATTCTTC GGGCAAGAAA CAAGTTTGCT GATGCGCTTG       540
CTCTCTATGA GGCTATGCTG GAGAAAGATA GCAAGAATGT TGAAGCTCAC ATTGGAAAAG       600
GGATATGCTT GCAGACGCAG AACAAAGGGA ATCTAGCTTT CGATTGTTTT TCTGAAGCGA       660
TCAGGTTGGA TCCGCATAAT GCTTGTGCCC TTACACACTG TGGTATACTT CATAAAGAAG       720
AAGGACGCCT CGTAGAAGCT GCTGAGTCCT ACCAGAAAGC ATTGATGGCA GATGCATCAT       780
ACAAGCCAGC AGCAGAGTGT TTAGCCATTG TTTTGACCGA CCTTGGAACT AGCCTGAAGC       840
TGGCTGGGAA TACTCAGGAA GGAATTCAAA AGTATTACGA AGCCCTTAAG ATTGACCCAC       900
ACTATGCTCC TGCATATTAC AACTTAGGTG TTGTATACTC CGAAATGATG CAATATGACA       960
ATGCCTTGAG CTGCTACGAG AAGGCTGCAC TTGAGAGGCC TATGTATGCT GAAGCATATT      1020
GTAACATGGG TGTCATTTAT AAGAACCGTG GTGACTTGGA GATGGCAATC ACTTGTTATG      1080
AGAGATGTCT AGCTGTGTCT CCAAACTTTG AGATTGCGAA GAACAATATG GCCATAGCTC      1140
TGACAGATTT AGGAACAAAG GTTAAACTTG AAGGCGATGT AACCCAAGGA GTGGCATATT      1200
ACAAGAAGGC TCTCTATTAT AACTGGCACT ATGCAGATGC TATGTACAAT CTTGGGGTGG      1260
CTTATGGAGA AATGCTAAAG TTCGACATGG CGATTGTCTT CTATGAGCTT GCTTTCCACT      1320
TTAATCCACA TTGTGCTGAG GCTTGCAACA ATTTGGGAGT ACTTTACAAA GACCGTGACA      1380
ACCTTGATAA AGCTGTGGAG TGTTATCAGA TGGCTCTATC AATCAAACCA AATTTTGCAC      1440
AGTCGCTTAA TAACCTTGGT GTCGTCTATA CAGTCCAGGG GAAAATGGAT GCTGCTGCCA      1500
GCATGATTGA GAAGGCTATA CTTGCTAATC CCACATATGC AGAAGCTTTT AACAACCTAG      1560
GTGTTCTTTA CAGAGATGCT GGAAATATAA CTATGGCTAT CGATGCTTAT GAGGAATGCC      1620
TTAAGATAGA TCCAGATTCT CGCAATGCTG GCCAGAACCG ATTGCTTGCC ATGAATTACA      1680
TAAATGAAGG ACTCGATGAC AAACTATTTG AGGCTCACAG AGACTGGGGT TGGCGCTTCA      1740
CAAGATTACA CCCTCAATAC ACTTCATGGG ATAATCTGAA AGATCCAGAG CGACCTATCA      1800
CCATTGGATA TATCTCACCA GATTTCTTCA CTCATTCAGT ATCTTATTTC ATTGAAGCTC      1860
CCCTTACGCA TCATGATTAT ACAAAGTACA AAGTGGTGGT TTATTCAGCG GTAGTTAAGG      1920
CAGATGCAAA AACATACAGG TTTAGGGATA AAGTGTTGAA GAAAGGTGGA GTTTGGAAGG      1980
ATATATACGG GATAGATGAG AAAAAGATAG CAAGTATGGT CAGAGAGGAC AAAATCGACA      2040
TTTTGGTAGA ACTCACTGGT CATACGGCAA CAACAAGTT GGGAACAATG GCCTGCAGAC      2100
CAGCACCGGT TCAGGTTACT TGGATCGGCT ATCCAAATAC TACGGGTTTG CCCACTGTTG      2160
ATTACAGAAT TACAGATTCG TTGGCTGATC CACCAGATAC CAAACAAAAG CAGGTCGAGG      2220
AGCTGGTTAG GCTTCCGGAC TGTTTTCTTT GTTATACACC TTCCCAGAG GCTGGTCCTG       2280
TTTGTCCAAC ACCTGCGCTT TCTAATGGCT TTGTCACATT TGGTAGTTTC AACAACCTCG      2340
```

-continued

```
CAAAGATAAC TCCTAAGGTG CTGCAAGTGT GGGCTAGGAT ACTGTGTGCA GTTCCCAATT    2400

CTCGTCTAGT GGTAAAATGC AAACCTTTCT GCTGCGATAG CATTAGGCAG AGGTTTCTCA    2460

CCACGCTGGA GCAGCTTGGG TTAGAATCAA AGCGTGTTGA TCTCTTGCCT CTGATTCTTT    2520

TCAATCACGA CCATATGCAA GCCTATTCCT TGATGGATAT TAGTTTGGAC ACATTCCCTT    2580

ATGCTGGAAC TACCACTACC TGTGAGTCTC TCTACATGGG AGTTCCATGT GTTACAATGG    2640

CTGGCTCAGT ACATGCTCAT AATGTTGGTG TCAGTCTTCT CACTAAAGTT GGATTAGGAC    2700

ACCTGGTTGC CAAAAATGAG GATGAGTATG TTCAGCTATC TGTTGATCTA GCCTCTGATG    2760

TCACAGCTCT TTCTAAATTG AGAATGAGTC TCCGGGATCT AATGGCTGGA TCTCCTGTTT    2820

GTAATGGTCC TTCCTTTGCT GTTGGTCTTG AATCCGCATA TCGGAATATG TGGAAAAAGT    2880

ACTGCAAAGG TGAAGTGCCG TCCTTAAGGC GAATGGAAAT GCTGCAAAAA GAGGTCCATG    2940

ATGATCCCTT AATCTCAAAA GACTTGGGAC CATCAAGAGT CAGCGTTACT GGAGAAGCCA    3000

CTCCGTCTCT CAAGGCCAAT GGTTCTGCTC CTGTACCTTC CTCTTTACCA ACCCAATCCC    3060

CGCAGCTCTC AAAGAGAATG GACTCCACTA GCTAGATAAC CAGCAAATCG AGCTGCTGCG    3120

AAATGCCGGC AGAGAGTCTT GACCCATCTG GAAAAGGTGT GAAAGAAAGA GTCGATGAGC    3180

TTTTCCTGCT ATTTACTTCC AAGACAATAG GAACTAGACT TTAGATTACT GCTTGTGTAG    3240

TAAAAAGAAT AGTAAAACCA GCTCTTTCTT TTGTTGTATC TCTTTCTACT CTTAGTTTAG    3300

CTTTACATGA TTCTTGGGAA GTCGTTAGGT GGTAGTGGAT TTGGAGTTTT TCTTCTCATT    3360

TGAGAGATCA AGTTGTTGTG TATCGATTAG GGTTTTAAGG CTTTTTAGGA TGTTTTCATG    3420

TGTTGGATTT TGACTCATAT GATAGTAAAT ATAGTTATAG AAAGCTTTTC GGTGCC        3476
```

(2) INFORMATION FOR SEQ ID NO:2:

(i) SEQUENCE CHARACTERISTICS:
        (A) LENGTH: 981 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:2:

```
Ala Trp Arg Leu Arg Tyr Thr Asp Gln Arg Phe Leu Phe Ser Glu Glu
 1               5                  10                  15

Arg Gly Glu Ile Ser Phe Ser Tyr Val Tyr Ser Asn Ile Ser Phe Phe
                20                  25                  30

Phe Ser His Ser Ile Ser Ser Leu Ala Ala Pro Glu Val Ser Ser Leu
            35                  40                  45

Gln Ser Gln Val Pro Leu Phe Arg Phe Cys Gly Glu Gln Asp Phe Ser
        50                  55                  60

Cys Lys Lys Met Val Gly Leu Glu Asp Asp Thr Glu Arg Glu Arg Ser
65                  70                  75                  80

Pro Val Val Glu Asn Gly Phe Ser Asn Gly Ser Arg Pro Ser Ser Ser
                85                  90                  95

Ser Ala Gly Val Leu Ser Pro Ser Arg Lys Val Thr Gln Gly Asn Asp
            100                 105                 110

Thr Leu Ser Tyr Ala Asn Ile Leu Arg Ala Arg Asn Lys Phe Ala Asp
        115                 120                 125

Ala Leu Ala Leu Tyr Glu Ala Met Leu Glu Lys Asp Ser Lys Asn Val
    130                 135                 140

Glu Ala His Ile Gly Lys Gly Ile Cys Leu Gln Thr Gln Asn Lys Gly
145                 150                 155                 160
```

```
Asn Leu Ala Phe Asp Cys Phe Ser Glu Ala Ile Arg Leu Asp Pro His
            165                 170                 175

Asn Ala Cys Ala Leu Thr His Cys Gly Ile Leu His Lys Glu Glu Gly
        180                 185                 190

Arg Leu Val Glu Ala Ala Glu Ser Tyr Gln Lys Ala Leu Met Ala Asp
        195                 200                 205

Ala Ser Tyr Lys Pro Ala Ala Glu Cys Leu Ala Ile Val Leu Thr Asp
210                 215                 220

Leu Gly Thr Ser Leu Lys Leu Ala Gly Asn Thr Gln Glu Gly Ile Gln
225                 230                 235                 240

Lys Tyr Tyr Glu Ala Leu Lys Ile Asp Pro His Tyr Ala Pro Ala Tyr
                245                 250                 255

Tyr Asn Leu Gly Val Val Tyr Ser Glu Met Met Gln Tyr Asp Asn Ala
                260                 265                 270

Leu Ser Cys Tyr Glu Lys Ala Ala Leu Glu Arg Pro Met Tyr Ala Glu
            275                 280                 285

Ala Tyr Cys Asn Met Gly Val Ile Tyr Lys Asn Arg Gly Asp Leu Glu
        290                 295                 300

Met Ala Ile Thr Cys Tyr Glu Arg Cys Leu Ala Val Ser Pro Asn Phe
305                 310                 315                 320

Glu Ile Ala Lys Asn Asn Met Ala Ile Ala Leu Thr Asp Leu Gly Thr
                325                 330                 335

Lys Val Lys Leu Glu Gly Asp Val Thr Gln Gly Val Ala Tyr Tyr Lys
                340                 345                 350

Lys Ala Leu Tyr Tyr Asn Trp His Tyr Ala Asp Ala Met Tyr Asn Leu
            355                 360                 365

Gly Val Ala His Gly Glu Met Leu Lys Phe Asp Met Ala Ile Val Phe
        370                 375                 380

Tyr Glu Leu Ala Phe His Phe Asn Pro His Cys Ala Glu Ala Cys Asn
385                 390                 395                 400

Asn Leu Gly Val Leu Tyr Lys Asp Arg Asp Asn Leu Asp Lys Ala Val
                405                 410                 415

Glu Cys Tyr Gln Met Ala Leu Ser Ile Lys Pro Asn Phe Ala Gln Ser
            420                 425                 430

Leu Asn Asn Leu Gly Val Val Tyr Thr Val Gln Gly Lys Met Asp Ala
        435                 440                 445

Ala Ala Ser Met Ile Glu Lys Ala Ile Leu Thr Asn Pro Thr Tyr Ala
        450                 455                 460

Glu Ala Phe Asn Asn Leu Gly Val Leu Tyr Arg Asp Ala Gly Asn Ile
465                 470                 475                 480

Thr Met Ala Ile Asp Ala Tyr Glu Glu Cys Leu Lys Ile Asp Pro Asp
                485                 490                 495

Ser Arg Asn Ala Gly Gln Asn Arg Leu Leu Ala Met Asn Tyr Ile Asn
            500                 505                 510

Glu Gly Leu Asp Asp Lys Leu Phe Glu Ala His Arg Asp Trp Gly Trp
        515                 520                 525

Arg Phe Thr Arg Leu His Pro Gln Tyr Thr Ser Trp Asp Asn Leu Lys
530                 535                 540

Asp Pro Glu Arg Pro Ile Thr Ile Gly Tyr Ile Ser Pro Asp Phe Phe
545                 550                 555                 560

Thr His Ser Val Ser Tyr Phe Ile Glu Ala Pro Leu Thr His His Asp
                565                 570                 575

Tyr Thr Lys Tyr Lys Val Val Val Tyr Ser Ala Val Val Lys Ala Asp
```

-continued

```
                580                 585                 590
Ala Lys Thr Tyr Arg Phe Arg Asp Lys Val Leu Lys Lys Gly Gly Val
            595                 600                 605

Trp Lys Asp Ile Tyr Gly Ile Asp Glu Lys Lys Ile Ala Ser Met Val
        610                 615                 620

Arg Glu Asp Lys Ile Asp Ile Leu Val Glu Leu Thr Gly His Thr Ala
625                 630                 635                 640

Asn Asn Lys Leu Gly Thr Met Ala Cys Arg Pro Ala Pro Val Gln Val
                645                 650                 655

Thr Trp Ile Gly Tyr Pro Asn Thr Gly Leu Pro Thr Val Asp Tyr
            660                 665                 670

Arg Ile Thr Asp Ser Leu Ala Asp Pro Pro Asp Thr Lys Gln Lys Gln
            675                 680                 685

Val Glu Glu Leu Val Arg Leu Pro Asp Cys Phe Leu Cys Tyr Thr Pro
    690                 695                 700

Ser Pro Glu Ala Gly Pro Val Cys Pro Thr Pro Ala Leu Ser Asn Gly
705                 710                 715                 720

Phe Val Thr Phe Gly Ser Phe Asn Asn Leu Ala Lys Ile Thr Pro Lys
                725                 730                 735

Val Leu Gln Val Trp Ala Arg Ile Leu Cys Ala Val Pro Asn Ser Arg
                740                 745                 750

Leu Val Val Lys Cys Lys Pro Phe Cys Cys Asp Ser Ile Arg Gln Arg
            755                 760                 765

Phe Leu Thr Thr Leu Glu Gln Leu Gly Leu Glu Ser Lys Arg Val Asp
    770                 775                 780

Leu Leu Pro Leu Ile Leu Phe Asn His Asp His Met Gln Ala Tyr Ser
785                 790                 795                 800

Leu Met Asp Ile Ser Leu Asp Thr Phe Pro Tyr Ala Gly Thr Thr Thr
                805                 810                 815

Thr Cys Glu Ser Leu Tyr Met Gly Val Pro Cys Val Thr Met Ala Gly
            820                 825                 830

Ser Val His Ala His Asn Val Gly Val Ser Leu Leu Thr Lys Val Gly
        835                 840                 845

Leu Gly His Leu Val Ala Lys Asn Glu Asp Glu Tyr Val Gln Leu Ser
    850                 855                 860

Val Asp Leu Ala Ser Asp Val Thr Ala Leu Ser Lys Leu Arg Met Ser
865                 870                 875                 880

Leu Arg Asp Leu Met Ala Gly Ser Pro Val Cys Asn Gly Pro Ser Phe
                885                 890                 895

Ala Val Gly Leu Glu Ser Ala Tyr Arg Asn Met Trp Lys Lys Tyr Cys
            900                 905                 910

Lys Gly Glu Val Pro Ser Leu Arg Arg Met Glu Met Leu Gln Lys Glu
        915                 920                 925

Val His Asp Asp Pro Leu Ile Ser Lys Asp Leu Gly Pro Ser Arg Val
    930                 935                 940

Ser Val Thr Gly Glu Ala Thr Pro Ser Leu Lys Ala Asn Gly Ser Ala
945                 950                 955                 960

Pro Val Pro Ser Ser Leu Pro Thr Gln Ser Pro Gln Leu Ser Lys Arg
                965                 970                 975

Met Asp Ser Thr Ser
            980
```

(2) INFORMATION FOR SEQ ID NO:3:

(i) SEQUENCE CHARACTERISTICS:
    (A) LENGTH: 6479 base pairs
    (B) TYPE: nucleic acid
    (C) STRANDEDNESS: single
    (D) TOPOLOGY: linear (ii) MOLECULE TYPE: DNA (genomic)

(xi) SEQUENCE DESCRIPTION: SEQ ID NO:3:

```
GGATCCACTA GTTCTAGACT AGTTTCATAG TCCATGAAAA AAACATCAAA TCTCCTAAAT      60

GGCTGGACAT AATTCAGATG ATTTTGTATG AAATAAAACA TAAAACATAT ATTTTCTTGC     120

ATATCTGGAG ATTTTTGTTT CTTTATTACA ATGACTAATT AATTTACCTT GTTCCTTTTT     180

ATTTTTGCAA AATGATTACT GTTATCTATT TTGTCCGTTT CTAATAAAAT AAAATAACAA     240

TCTGAGCTGT GGAAAGAAAA AAAAAGGAAA AGCGAGGAGA GCTAATCTGA GTCGTTGCCT     300

CTGTCCACTG GCTCGGACCG ACCTCGTACC TCTTTCATTT GTCCTCGAGC TTATAATAGA     360

CGTACGCCGT CGCCGCCACC TCCGCTCCAT CCATTCACGG CCAAGCGACG ACTCCACCGC     420

TTAGGCTTGG CGTCTGAGGT ATACTGATCA ACGCTTTCTG TTTTCGGAGG AGCGAGGCGA     480

GATCAGCTTC TCTTATGTCT ACTCAAACAT ATCATTCTTC TTTAGCCACT CGATTTCTTC     540

TCTAGCGGCT CCAGAGGTTT CGTCGCTACA GAGTCAAGTT CCTCTTTTCA GGTTTTGTGG     600

TAAGTAATCG TTAAACCCTA AGTATCGGAC CTTGTTGTTT AATCTGTTCG TGTTTACTCT     660

CAATTACATA TGCATTCTTC TGCTTAATCG TTTCTTTTAG TTTAATTTCT AGGGTTTACA     720

TCCCAAAGGT CTGATCTTTT TGCATATTTG TGTGAATCTT AGTTTTTTTT TTTTTTTTTG     780

GAATTGAATG TGATGAGTTG GGTTTGATAC TGTTAAAGAT CAAATCTTTA GCTTCGTTGA     840

AGCTTCATAT TTATGTCAAC AATGCAAGGT TTATTTTTCT TCCACCTTTG ATTTGATATT     900

TATAATTGTT TCTTTGAAGG TGAACAAGAT TTTAGTTACA AAAAAATGGT GGGACTGGAA     960

GATGATACTG AGAGAGAGAG GTCACCAGTC GTAGAGAATG GTTTTTCCAA TGGGTCTCGG    1020

TCTTCTTCTT CTAGCGCAGG TGTTTTGTCT CCATCACGAA AGGTCACTCA GGGGAACGAT    1080

ACACTTTCTT ATGCCAATAT TCTTCGGGCA AGAAACAAGT TTGCTGATGC GCTTGCTCTC    1140

TATGAGGCTA TGCTGGAGAA AGATAGCAAG AATGTTGAAG CTCACATTGG AAAAGGGATA    1200

TGCTTGCAGA CGCAGAACAA AGGGAATCTA GCTTTCGATT GTTTTTCTGA AGCGATCAGG    1260

TTGGATCCGC ATAATGCTTG TGCCCTTACA CACTGTGGTA TACTTCATAA AGAAGAAGGA    1320

CGCCTCGTAG AAGCTGCTGA GGTGCAACAT TACATTACCT TCTATCTGTG ATGATTTGCA    1380

TTAGAGGGTG CTGCATTAGT TAGACCATTG AACTTGTTAA ATTGGTGATA TGCAATTATG    1440

CATTAGGTTT TTTGCTAGGT AATCAGTTTC TAACGATTAA TCATCATATT TTGCACAGTC    1500

CTACCAGAAA GCATTGATGG CAGATGCATC ATACAAGCCA GCAGCAGAGT GTTTAGCCAT    1560

TGTTTTGACC GACCTTGGAA CTAGCCTGAA GCTGGCTGGG AATACTCAGG AAGGAATTCA    1620

AAAGTATTAC GAAGCCCTTA AGATTGACCC ACACTATGCT GTAATTTTCT GTTCCTCTAC    1680

CATTTCACAC TCTTGGTACC ATTTAACTGA TTCTCTAATT CAGTATGTTA TAATATATTT    1740

ATGCAGCCTG CATATTACAA CTTAGGTGTT GTATACTCCG AAATGATGCA ATATGACAAT    1800

GCCTTGAGCT GCTACGAGAA GGCTGCACTT GAGAGGCCTA TGTATGCTGA AGCATATTGT    1860

AACATGGGTG TCATTTATAA GAACCGTGGT GACTTGGAGA TGGCAATCAC TTGTTATGAG    1920

AGGTAGCATA TCTGTTAATT CATCTCTAAC TGTTGACTGG TTTCTTGCTA CTTTGTTGAA    1980

CGTGCAAGTA AGGCGCTGAT TTTTTTCTCT TCTTCTTCTG CCTTTAGATG TCTAGCTGTG    2040

TCTCCAAACT TTGAGATTGC GAAGAACAAT ATGGCCATAG CTCTGACAGA TTTAGGAACA    2100
```

```
AAGGTAAGAA TCCTTAAATT TTATCACAAT TTATAACTCA AGTATACTTT TTGTAAGGGG    2160

CGCCTTCTGG AAAATTCGTT ATAAAACTTC GTTTTGTTTA GCTCCCCTTT GTGCTGTGTG    2220

TGCTTTGTAC TTATGTCACG GCAATGGCAT TGGAATCTGT TTATGTTCTT TACTAGTGAA    2280

CTTTTGCGCT GAATAATTTT GATTTGCAGT TTCTTAATCC TTCTTTTCCA TTGGCGAGAA    2340

GCTGTTCAGC TGTGAGTACA TCTGACTTGT CAAATGTCAA TGATATTTCA GGTTAAACTT    2400

GAAGGCGATG TAACCCAAGG AGTGGCATAT TACAAGAAGG CTCTCTATTA TAACTGGCAC    2460

TATGCAGATG CTATGTACAA TCTTGGGGTG GCTTATGGAG AAATGCTAAA GTTCGACATG    2520

GTATTTAATT TGTGATTTGT TCATTTCTGT AAGTCAGTAA TGGTGTGGTT GTTATCGCGT    2580

GTTTATCCTT TCCTCGCCAC TTTACTCGCT TGATAAAATG ATATATATCT TGACTAGTTT    2640

ATCTACCTAG ATTTTTATCC TTCTCCACAT GTTCTCGTAA TTAATCCAAA ACTCTGTATG    2700

TAGATCTCTA TATTATAATG GAATTGTAGA GCCAAAGAAT GAAATATGTC TGTGGTCATG    2760

ATTGCATTCT CAATGTGCAG GCGATTGTCT TCTATGAGCT TGCTTTCCAC TTTAATCCAC    2820

ATTGTGCTGA GGCTTGCAAC AATTTGGGAG TACTTTACAA AGACCGTGAC AACCTTGATA    2880

AAGCTGTGGA GTGTTATCAG GTAATATTTT TGCAGATATC TGTAGCGTTT CATGAGAATT    2940

TCATTGTGTT TGGTGGCTTA TTATATCTCC CAACCTATGT AGATGGCTCT ATCAATCAAA    3000

CCAAATTTTG CACAGTCGCT TAATAACCTT GGTGTCGTCT ATACAGTCCA GGTTTGATAT    3060

ATATTAAGGG CGGCTTAATG TTTTCTTAAT TGAATCTCCT AAGTCGATAG AATGCCAATT    3120

CCTCTGATAT TACAGGGGAA AATGGATGCT GCTGCCAGCA TGATTGAGAA GGCTATACTT    3180

GCTAATCCCA CATATGCAGA AGCTTTTAAC AACCTAGGTC TGTTTTCTCA TCTTCTGTTC    3240

TTTACGAGCT TCCTCACGTG TTACAACTGC TTAGAAACTA TATTCCTTTG AAATTTAGAT    3300

TTTATGTTTG TCCTTTTGTT TCTACCTCCC TGGCGCTAAG AGTCTTGTAG TGTCTGTGAT    3360

AACCAGTTTC ATGGTGCGAT TCAAATGTAG GTGTTCTTTA CAGAGATGCT GGAAATATAA    3420

CTATGGCTAT CGATGCTTAT GAGGAATGCC TTAAGATAGA TCCAGATTCT CGCAATGCTG    3480

GCCAGGTATC TATACTTTAG CGTGGTCTTC TTGTTATGAG GTTGAAAGAT ATATGTGTTT    3540

AAAACCTTCT TGTCCCCTTT TGTAGAACCG ATTGCTTGCC ATGAATTACA TAAATGAAGG    3600

ACTCGATGAC AAACTATTTG AGGCTCACAG GTAAGCACAT ATATTATTAA TGTAGATTTG    3660

TATTATGTTG CTTTTATGGG TCTTACAGTG AAAAAATCTT CTGAACACAG AGACTGGGGT    3720

TGGCGCTTCA CAAGATTACA CCCTCAATAC ACTTCATGGG ATAATCTGAA AGATCCAGAG    3780

CGACCTATCA CCATTGGATA TATCTCACCA GATTTCTTCA CTCATTCAGT ATCTTATTTC    3840

ATTGAAGCTC CCCTTACGCA TCATGATTAT ACAAAGTACA AAGTGGTGGT TTATTCAGCG    3900

GTAGTTAAGG TAGGATTTTT ACCTATATAA CTTATATAGA TACATTTTCC CTCTAAGCAA    3960

TTCATTTCCT GGTTCTCGTG GCATTTTTCC CTTTTGAGCA ATCATTGGTC TCTCATGGCT    4020

TTGCAGGCAG ATGCAAAAAC ATACAGGTTT AGGGATAAAG TGTTGAAGAA AGGTGGAGTT    4080

TGGAAGGATA TATACGGGAT AGATGAGAAA AAGATAGCAA GTATGGTCAG AGAGGACAAA    4140

ATCGACATTT TGGTAGAACT CACTGGTCAT ACGGCAAACA ACAAGTTGGG AACAATGGCC    4200

TGCAGACCAG CACCGGTTCA GGTGAGAGGA TATATTAAAC CTATCTCATT TTGTTGTTTC    4260

GGGTTTTGCC TTTGACTTTC CATTTCAAGT GTACTTATAT TGGCTAAGAT ACCAGGTTAC    4320

TTGGATCGGC TATCCAAATA CTACGGGTTT GCCCACTGTT GATTACAGAA TTACAGATTC    4380

GTTGGCTGAT CCACCAGATA CCAAACAAAA GTACGTTTTG GTTCAAGATG CAATTTTGGG    4440

TTTCGGAAGT GCTCCAAATA AAAATCTTAA TTTTTATTTA TTTATTTTGT GATATTTGAT    4500
```

```
TGCAGGCAGG TCGAGGAGCT GGTTAGGCTT CCGGACTGTT TTCTTTGTTA TACACCTTCC    4560

CCAGAGGCTG GTCCTGTTTG TCCAACACCT GCGCTTTCTA ATGGCTTTGT CACATTTGGT    4620

AGTTTCAACA ACCTCGCAAA GGTTAAAAAA TTTGTGTCCT TGGATTATGC ACACCAATCT    4680

CCCCTAGTAT CTCTTTCAAT GTTTTGACAG GTTTATCTCT GTTTGTGCAA ATCAGATAAC    4740

TCCTAAGGTG CTGCAAGTGT GGGCTAGGAT ACTGTGTGCA GTTCCCAATT CTCGTCTAGT    4800

GGTAAAATGC AAACCTTTCT GCTGCGATAG CATTAGGCAG AGGTTTCTCA CCACGCTGGA    4860

GCAGCTTGGG TTAGAATCAA AGCGTGTTGA TCTCTTGCCT TTGATTCTTT TCAATCACGA    4920

CCATATGCAA GCCTATTCCT TGATGGATAT TAGGTAAGAT TTGACACATA GTGCTCTGTA    4980

AAACACCGAG GCTTATAGAT TCACATATTT AATTTACATT TATTGCAGTT TGGACACATT    5040

CCCTTATGCT GGAACTACCA CTACCTGTGA GTCTCTCTAC ATGGGAGTTC CATGTGTTAC    5100

AATGGCTGGC TCAGTACATG CTCATAATGT TGGTGTCAGT CTTCTCACTA AGTTGGTAA    5160

GCTCTTAGCA AAATTTTTTT TTTTTTTTTT GCAAAAATTG TTGTTAGTCG ACATCTTTTA    5220

GCTAATTCAG CCATTTCTTG ATTCAGGATT AGGACACCTG GTTGCCAAAA ATGAGGATGA    5280

GTATGTTCAG CTATCTGTTG ATCTAGCCTC TGATGTCACA GCTCTTTCTA AATTGAGAAT    5340

GAGTCTCCGG GATCTAATGG CTGGATCTCC TGTTTGTAAT GGTCCTTCCT TTGCTGTTGG    5400

TCTTGAATCC GCATATCGGA ATATGTGGAA AAAGTACTGC AAAGGTGAAG TGCCGTCCTT    5460

AAGGCGAATG GAAATGCTGC AAAAAGAGGT CCATGATGAT CCCTTAATCT CAAAAGACTT    5520

GGGACCATCA AGAGTCAGCG TTACTGGAGA AGCCACTCCG TCTCTCAAGG CCAATGGTTC    5580

TGCTCCTGTA CCTTCCTCTT TACCAACCCA ATCCCCGCAG CTCTCAAAGA GAATGGACTC    5640

CACTAGCTAG ATAACCAGCA AATCGAGCTG CTGCGAAATG CCGGCAGAGA GTCTTGACCC    5700

ATCTGGAAAA GGTGTGAAAG AAAGAGTCGA TGAGCTTTTC CTGCTATTTA CTTCCAAGAC    5760

AATAGGAACT AGACTTTAGA TTACTGCTTG TGTAGTAAAA AGAATAGTAA AACCAGCTCT    5820

TTCTTTTGTT GTATCTCTTT CTACTCTTAG TTTAGCTTTA CATGATTCTT GGGAAGTCGT    5880

TAGGTGGTAG TGGATTTGGA GTTTTTCTTC TCATTTGAGA GATCAAGTTG TTGTGTATCG    5940

ATTAGGGTTT TAAGGCTTTT TAGGATGTTT TCATGTGTTG GATTTGACT CATATGATAG    6000

TAAATATAGT TATAGAAAGC TTTTCGGTGC CTTTACCTAT TTCATAATAT AATTATCTAA    6060

AACTCCTGCT TAAGCTTAAT CCCATAGGTG AGACCCAATG AAAGACTTTT GACTTGTATG    6120

ATTATGTTGC CAACTCCATA TCTCTCTTTA ATTAATTAAT ATGGAGAGAG TAAAAAGGCA    6180

AGCAACTAAC TACTCTTCAA TTCAACACTT CTTCTGCTCC ATTGCTTCCA CCAGAACCCT    6240

AAAGACCTTA TAAAACCCAA TCCCAAATCC CTTTGCTCAT TCACCACCAA AGCATCCAAC    6300

TTTCTTTGCT TCCTCTTTCA AAGCAACACA AAATATTAAA TCTCAAGAAA CAAAGTAAAG    6360

AAAAATGAAG AACGAATCTA CCTTCATTGA TGTCCCTGCA GAATCCAGCT CAGCCATGAA    6420

AGGCAAAGCT CCTCTAATCG GTGTAGCAAG AGACCACACT ACTAGTGGCT CAGGTGGAT    6479
```

(2) INFORMATION FOR SEQ ID NO:4:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:4:

```
CTTCTCTTAT GTCTACTCAA                                                   20
```

(2) INFORMATION FOR SEQ ID NO:5:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:5:

TGTTGAAGCT CACATTGGAA      20

(2) INFORMATION FOR SEQ ID NO:6:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:6:

CACAGCTTTA TCAAGGTT      18

(2) INFORMATION FOR SEQ ID NO:7:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:7:

GGCCATAGCT CTGACA      16

(2) INFORMATION FOR SEQ ID NO:8:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:8:

GAGAAATGCT AAAGTTCGAC AT      22

(2) INFORMATION FOR SEQ ID NO:9:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:9:

TACAGAGATG CTGGAA      16

(2) INFORMATION FOR SEQ ID NO:10:

(i) SEQUENCE CHARACTERISTICS:

-continued

```
        (A) LENGTH: 19 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:10:

GCAGCAGAAA GGTTTGCAT                                                  19

(2) INFORMATION FOR SEQ ID NO:11:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:11:

ATCCAAATAC TACGGGTT                                                   18

(2) INFORMATION FOR SEQ ID NO:12:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:12:

CTTTCACACC TTTTCCAGAT                                                 20

(2) INFORMATION FOR SEQ ID NO:13:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:13:

GAGATCCAGC CATTAGAT                                                   18

(2) INFORMATION FOR SEQ ID NO:14:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:14:

GCTTTCCACT TTAATCCACA T                                               21

(2) INFORMATION FOR SEQ ID NO:15:

(i) SEQUENCE CHARACTERISTICS:
        (A) LENGTH: 20 base pairs
        (B) TYPE: nucleic acid
        (C) STRANDEDNESS: single
        (D) TOPOLOGY: linear
```

```
       (ii) MOLECULE TYPE: DNA (genomic)

(xi) SEQUENCE DESCRIPTION: SEQ ID NO:15:

GAAGATGAGA AAACAGACCT                                                    20
```